United States Patent
Zack et al.

(10) Patent No.: US 11,274,315 B2
(45) Date of Patent: Mar. 15, 2022

(54) CHIMERIC INSECTICIDAL PROTEINS

(71) Applicant: CORTEVA AGRISCIENCE LLC, Indianapolis, IN (US)

(72) Inventors: Marc D Zack, Zionsville, IN (US); Megan Sopko, Zionsville, IN (US); James M Hasler, Danville, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

(21) Appl. No.: 16/650,300

(22) PCT Filed: Sep. 26, 2018

(86) PCT No.: PCT/US2018/052788
§ 371 (c)(1),
(2) Date: Mar. 24, 2020

(87) PCT Pub. No.: WO2019/067496
PCT Pub. Date: Apr. 4, 2019

(65) Prior Publication Data
US 2020/0318132 A1 Oct. 8, 2020

Related U.S. Application Data

(60) Provisional application No. 62/563,228, filed on Sep. 26, 2017.

(51) Int. Cl.
*C12N 15/82* (2006.01)
*C07K 14/32* (2006.01)
*C07K 14/325* (2006.01)

(52) U.S. Cl.
CPC ........ *C12N 15/8286* (2013.01); *C07K 14/325* (2013.01)

(58) Field of Classification Search
None
See application file for complete search history.

(56) References Cited

U.S. PATENT DOCUMENTS

| | | |
|---|---|---|
| 7,129,212 B2 | 10/2006 | Narva et al. |
| 2005/0210545 A1 | 9/2005 | Shen et al. |
| 2010/0004176 A1* | 1/2010 | Sampson ............... A01N 37/18 514/4.5 |
| 2013/0203657 A1 | 8/2013 | Meade et al. |
| 2015/0299274 A1 | 10/2015 | Sampson et al. |

FOREIGN PATENT DOCUMENTS

| | | |
|---|---|---|
| WO | 2013/122720 | 8/2013 |
| WO | 2014/126986 | 8/2014 |

OTHER PUBLICATIONS

International Search Report and Written Opinion for International Application No. PCT/US18/52788, dated Jan. 28, 2019.
Supplemental European Search Report and Search Opinion for EP 18863513, dated Apr. 12, 2021.

* cited by examiner

*Primary Examiner* — Matthew R Keogh

(57) ABSTRACT

IRDIG35563 vegetative insecticidal toxins, polynucleotides encoding such toxins, use of such toxins to control pests, and transgenic plants that produce such toxins are disclosed. The invention includes IRDIG35563 variants, fragments and analogs.

15 Claims, No Drawings
Specification includes a Sequence Listing.

CHIMERIC INSECTICIDAL PROTEINS

CROSS-REFERENCE TO RELATED APPLICATIONS

This Application is a national stage patent application of International patent application no. PCT/US2018/052788 filed Sep. 26, 2018, which claims the benefit of priority to U.S. Provisional Application No. 62/563,228 filed on Sep. 26, 2017, the disclosures of each of which are incorporated herein by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named "80144_WO_PCT_Sequence_Listing_ST25" created on Sep. 25, 2018, and having a size of 17 kilobytes and is filed concurrently with the specification. The sequence listing contained in this ASCII formatted document is part of the specification and is herein incorporated by reference in its entirety.

FIELD OF THE INVENTION

This invention generally relates to the field of molecular biology. More specifically the invention concerns new insecticidal protein toxins developed from vegetative insecticidal protein toxins found in *Bacillus thuringiensis* and their use to control insects.

BACKGROUND OF INVENTION

Insects and other pests cost farmers billions of dollars annually in crop losses and expense to keep these pests under control. In addition to losses in field crops, insect pests are also a burden to vegetable and fruit growers, to producers of ornamental flowers, and to home gardeners. The losses caused by insect pests in agricultural production environments include decrease in crop yield, reduced crop quality, and increased harvesting costs.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other beneficial insects. Another problem resulting from the wide use of chemical pesticides is the appearance of resistant insect populations. This has been partially alleviated by various resistance management practices, but there is an increasing need for alternative pest control agents. Biological pest control agents, such as *Bacillus thuringiensis* (Bt) strains expressing pesticidal toxins like delta-endotoxins, have also been applied to crop plants with satisfactory results, offering an alternative or compliment to chemical pesticides. The genes coding for some of these delta-endotoxins have been isolated and their expression in heterologous hosts have been shown to provide another tool for the control of economically important insect pests. In particular, the expression of insecticidal toxins, such as *Bacillus thuringiensis* delta-endotoxins, in transgenic plants have provided efficient protection against selected insect pests, and transgenic plants expressing such toxins have been commercialized, allowing farmers to reduce applications of chemical insect control agents.

The soil microbe *Bacillus thuringiensis* is a Gram-positive, spore-forming bacterium characterized by parasporal crystalline protein inclusions. *Bacillus thuringiensis* continues to be the leading source of novel insecticidal proteins for development of plant incorporated pesticides. In the North American maize insect resistance market, *Spodoptera frugiperda* (fall armyworm "FAW"), *Ostrinia* nubialis Hubner (European corn borer "ECB"), and *Helicoverpa zea* Boddie (corn earworm "CEW") are key driver pests, although there are other key insect pests in other geographies (e.g. *Helicoverpa armigera* (cotton bollworm "CBW" or corn earworm "CEW")) and additional secondary, but important insect pest species. Bt toxins represent over 90% of the bioinsecticide products commercially marketed and essentially the entire source of genes for transgenic crops that have been developed to provide resistance to insect feeding. Bt bacteria produce insecticidal delta-endotoxins including Crystal (Cry), Cytotoxin (Cyt), and Vegetative Insecticidal Protein (VIP) toxins, depending on their gene and protein structure. Cry toxins are produced during spore formation as insoluble crystal proteins. VIP toxins, on the other hand, are produced as soluble proteins during the vegetative stage of Bt bacterial growth. VIP proteins are distinct from Cry proteins in their structure, but share the property with Cry toxins of being pore formers acting on cells located in the insect midgut. The classification of VIP protein was previously based on their target insect types. Nomenclature is currently employed that systematically classifies the VIP genes based upon amino acid sequence homology rather than upon insect specificities. Crickmore, N., Baum, J., Bravo, A., Lereclus, D., Narva, K., Sampson, K., Schnepf, E., Sun, M. and Zeigler, D. R. "*Bacillus thuringiensis* toxin nomenclature" (2016); http://www.btnomenclature.info/; and http://www.lifesci.sussex.ac.uk/home/Neil_Crickmore/Bt/vip.html The continued use of chemical and biological agents to control insect pests heightens the chance for insects to develop resistance to such control measures. Also, the high selectivity of biological control agents often results in only a few specific insect pests being controlled by each agent. Despite the success of ECB-resistant transgenic corn, the possibility of the development of resistant insect populations threatens the long-term durability of Cry proteins in ECB control and creates the need to discover and develop new Cry or other types of biological control agents to control ECB and other pests.

There remains a need to discover and develop new and effective pest control agents that provide an economic benefit to farmers and that are environmentally acceptable. Particularly needed are control agents targeted to a wide spectrum of economically important insect pests that efficiently control insect populations that are, or could become, resistant to existing insect control agents and those with equal to or increased potency compared to current control agents.

BRIEF SUMMARY OF THE INVENTION

The present invention provides insecticidal chimeric VIP toxins, including the protein toxin designated as IRDIG35563 (SEQ ID NO:2) that was constructed based on the first 613 amino acid residues of VIP3Ab1 and a C-terminal portion of another VIP toxin, variants of IRDIG35563, nucleic acids encoding these chimeric toxins, methods of controlling pests using the toxins, methods of producing the toxins in transgenic host cells, and transgenic plants that express the toxins. The invention further provides a recombinant nucleic acid construct comprising one or more heterologous regulatory elements that drive expression of a nucleic acid sequence encoding SEQ ID NO:2 and nucleic acid sequences chosen from the group consisting of SEQ ID NO:1, SEQ ID NO:3, and SEQ ID NO:4. In another embodiment, the invention provides nucleic acid constructs comprising a nucleotide sequence that encodes an IRDIG35563 chimeric insect toxin operably linked to one or more regulatory regions such as a promoter that is not derived from Bt and is capable of driving expression in a host cell, preferably a plant cell. The invention includes an insecticidal chimeric toxin comprising residues 1 to 789 of SEQ ID NO:2, and plants or plant parts comprising such nucleic acid constructs. The invention further provides plants or plant parts wherein the chimeric toxin has insecticidal activity against insects selected from the group consisting of *Spodoptera exigua* (Beet armyworm, BAW), *Spodoptera eridania* (Southern armyworm, SAW), *Spodoptera frugiperda* (Fall armyworm, FAW), Cry1F resistant *Spodoptera frugiperda* (rFall armyworm, rFAW), *Helicoverpa zea* (Corn earworm, CEW), *Pseudoplusia includens* (Soybean looper, SBL), *Anticarsia gemmatalis* (Velvetbean caterpillar, VBC), *Heliothis virescens* (Tobacco budworm, TBW), and *Helicoverpa armigera* (Cotton bollworm, CBW). Also provided by the invention is a method for controlling susceptible insects comprising contacting the gut of said insect with an effective amount of a disclosed chimeric toxin as well as a method for controlling an insect pest population comprising contacting the gut of individuals of said pest population with a insecticidally effective amount of a disclosed chimeric toxin. Also provided is a method for producing an insect resistant or insect tolerant plant comprising breeding a non-transgenic plant with a transgenic plant comprising a disclosed DNA construct stably incorporated into the genome of the plant and selecting progeny contain the disclosed nucleic acid construct.

DESCRIPTION OF THE SEQUENCES

SEQ ID NO:1 A chimeric DNA sequence encoding IRDIG35563.
SEQ ID NO:2 The chimeric protein toxin sequence of IRDIG35563.
SEQ ID NO:3 A maize optimized High GC content DNA sequence encoding IRDIG35563.
SEQ ID NO:4 A soybean most preferred codon optimized DNA sequence encoding IRDIG35563.

DETAILED DESCRIPTION OF THE INVENTION

Definitions

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

"Sufficiently identical" is used herein to refer to an amino acid sequence that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to a reference sequence using one of the alignment programs described herein using standard parameters.

As used herein, the term "protein," "peptide molecule," or "polypeptide" includes those molecules that undergo modification, including post-translational modifications, such as, but not limited to, disulfide bond formation, glycosylation, phosphorylation or oligomerization.

The terms "amino acid" and "amino acids" refer to all naturally occurring L-amino acids.

"Retains insecticidal activity" is used herein to refer to a polypeptide having at least about 10%, at least about 30%, at least about 50%, at least about 70%, 80%, 90%, 95% or higher of the insecticidal activity of the full-length IRDIG35563 polypeptide.

"Fragments" or "biologically active portions" include polypeptide fragments comprising amino acid sequences sufficiently identical to an IRDIG35563 polypeptide and have insecticidal activity and polynucleotides encoding the fragments. "Fragments" or "biologically active portions" of IRDIG35563 polypeptides includes fragments comprising amino acid sequences sufficiently identical to the amino acid sequence set forth in IRDIG35563 polypeptides of the disclosure, wherein the polypeptide has insecticidal activity.

An "isolated" nucleic acid molecule (or DNA) is used herein to refer to a nucleic acid sequence (or DNA) that is no longer in its natural environment and have been placed in a difference environment by the hand of man, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived.

"Contiguous nucleotides" is used herein to refer to nucleotide residues that are immediately adjacent to one another.

As used herein non-genomic nucleic acid sequence, nucleic acid molecule or polynucleotide refers to a nucleic acid molecule that has one or more change in the nucleic acid sequence compared to a native or genomic nucleic acid sequence. In some embodiments, the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence.

The present invention provides insecticidal protein toxins and methods for delivering the toxins that are functionally active and effective against many orders of insects, especially Lepidopteran insects. By "functional activity" "functional" "insecticidal" or "active against" it is meant that the protein is functional as an orally active toxin or insect control agent, that the protein has a toxic effect, or is able to disrupt or deter insect growth or feeding. When an insect ingests an effective amount of a toxin of the subject invention delivered via transgenic plant expression, formulated protein composition(s), sprayable protein composition(s), a bait matrix or other delivery system, the results are typically death of the insect, inhibition of the growth or proliferation of the insect, or prevention of the insects from feeding upon the source, preferably a transgenic plant, that makes the toxins available to the insects. Functional proteins of the subject invention can also work together or alone to enhance or improve the activity of one or more other toxin proteins. The terms "toxic," "toxicity," or "toxin" are meant to convey that the subject toxins have functional activity as defined herein.

Complete lethality to feeding insects is preferred but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

Using various strains of bacterial isolates, we have invented new chimeric toxins that are active against an unexpectedly large array of commercially important insect pests. We describe here the invention of new chimeric VIP toxins that have unexpectedly broad spectrum insecticidal activity, including insecticidal activity against *Spodoptera exigua* (Beet armyworm, BAW), *Spodoptera eridania* (Southern armyworm, SAW), *Spodoptera frugiperda* (Fall armyworm, FAW) and FAW resistant to deregulated plant incorporated protectants, *Helicoverpa zea* (Corn earworm, CEW), *Pseudoplusia includens* (Soybean looper, SBL), *Anticarsia gemmatalis* (Velvetbean caterpillar, VBC), *Heliothis virescens* (Tobacco budworm, TBW), and *Helicoverpa armigera* (Cotton bollworm, CBW).

A class of insecticidal proteins called VIP3 has been described. See, e.g., Estruch et al. (1996, Proc. Natl. Acad. Sci. 93:5389-5394) and Yu et al. (1997, Appl. Environ. Microbiol. 63:532-536). VIP3 genes encode approximately 88 kDa proteins that are expressed by Bts during vegetative stages of growth. These toxins were reported to be distinct from crystal-forming delta-endotoxins. Reference to VIP toxins designated VIP1A(a), VIP1A(b), VIP2A(a), VIP2A (b), VIP3A(a), and VIP3A(b) is known in the literature. See also Lee et al., AEA/vol. 69, no. 8 (August 2003), pages 4648-4657, for a discussion of the mechanism of action and truncation of VIP proteins.

VIP3A protein toxins possess insecticidal activity against many lepidopteran pests, including FAW, CEW, *Agrotis Ipsilon* Hufnagel (black cutworm "BCW"), and *Heliothis virescens* Fabricius (tobacco budworm "TBW"). More recently, VIP proteins have been found to be toxic to certain species of hemipteran insect pests (Nanasaheb, P. et al, Toxins (Basel) vol. 4, no. 6 (June 2012), pages 405-429, Sattar S. and Maiti M. K., J. Microbiol. Biotechnol. 2011, 21:937-946). Thus, the VIP class of protein toxins display a unique spectrum of insecticidal activities. Other disclosures, WO 98/18932, WO 99/33991, WO 98/00546, and WO 99/57282, have also now identified homologues of the VIP3 class of proteins.

IRDIG35563 Polypeptides and Variants and Fragments there.

A novel VIP-based chimeric insecticidal protein, IRDIG35563, was created by combining the N-terminal 613 amino acids of VIP3Ab1 with the C-terminal 176 amino acids of IRDIG10870 (aka DIG740). Because of the redundancy of the genetic code, a variety of different nucleic acid sequences can encode the amino acid sequences disclosed herein. It is well within the skill of a person trained in the art to create these alternative nucleic acid sequences encoding the same, or essentially the same, toxins once the amino acid sequences are known.

Insect active variants of the IRDIG35563 toxin are also described herein, and are referred to collectively as IRDIG35563 insect toxins, or IRDIG35563 variants, and include truncated forms having N-terminal Met residues added to N-terminal truncations. IRDIG35563 variants are defined based on SEQ ID NO:2. For full length toxins, conservative amino acid substitutions varying no more than 5% from SEQ ID NO:2 that retain activity are within the scope of this invention.

In some embodiments, the IRDIG35563 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, as well as amino acid substitutions, deletions, insertions, fragments thereof, and combinations thereof. The term "about" when used herein in context with percent sequence identity means+/−0.5%. These values can be appropriately adjusted to determine corresponding homology of proteins considering amino acid similarity and the like.

In some embodiments, the sequence identity is against the full-length sequence of an IRDIG35563 polypeptide.

In some embodiments fragments of IRDIG35563 polypeptides comprise an amino acid sequence sufficiently identical to the amino acid sequence set forth in IRDIG35563 polypeptides of the disclosure, wherein the polypeptide has insecticidal activity. Such biologically active portions can be prepared by recombinant techniques and evaluated for insecticidal activity. In some embodiments, the IRDIG35563 polypeptide retains insecticidal activity against a Lepidopteran species. In some embodiments, the insecticidal activity is against one or more insect pests selected from BAW, SAW, FAW, rFAW, CEW, TBW, SBL, VBC, and CBW.

In some embodiments, the polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus, by proteolysis, or by insertion of a start codon, by deletion of the codons encoding the deleted amino acids and concomitant insertion of a start codon, and/or insertion of a stop codon in the sequence encoding the polypeptide fragment.

In some embodiments, the IRDIG35563 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 amino acids from the N-terminus of the IRDIG35563 polypeptide of SEQ ID NO: 2.

In some embodiments, the IRDIG35563 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to the IRDIG35563 polypeptide of SEQ ID NO: 2.

In some embodiments, an IRDIG35563 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the IRDIG35563 polypeptide of SEQ ID NO: 2, wherein the IRDIG35563 polypeptide has insecticidal activity.

A surprising property of IRDIG35563 is that it was found to be active against populations of FAW that have become resistant to certain Cry toxins, especially Cry1F. Accordingly, IRDIG35563 toxins are ideal candidates for control and prevention of resistant Lepidopteran pest populations. Another surprising property of IRDIG35563 toxins are their broad spectrum of activity against many Lepidopteran crop pests. Another surprising property of these chimeric toxins are their activity against Lepidopteran species that are pests of both maize and soybean including BAW, SAW, FAW, rFAW, CEW, TBW, SBL, VBC, and CBW.

IRDIG35563 toxins and insecticidally active variants. In addition to the full length IRDIG35563 toxin of SEQ ID NO:2, the invention encompasses insecticidally active variants of SEQ ID NO:2. By the term variant, applicants intend to include certain deletion, substitution, and insertion mutants. An IRDIG35563 fragment is any protein sequence that is found in SEQ ID NO:2 that is less than the full length IRDIG35563 amino acid sequence and which has insecticidal properties. IRDIG35563 variant fragments are also contemplated as part of the invention and are defined as fragments of IRDIG35563 containing certain deletion, substitution, and insertion mutants described herein and which have insecticidal activity.

IRDIG35563 Variants Created by Making a Limited Number of Amino Acid Deletions, Substitutions, or Additions.

Amino acid deletions, substitutions, and additions to the amino acid sequence of SEQ ID NO:2 can readily be made in a sequential manner and the effects of such variations on insecticidal activity can be tested by bioassay. The invention also includes insecticidally active variants of SEQ ID NO:2, in which up to 39 conservative independent amino substitutions have been made.

Amino acid sequence variants of an IRDIG35563 polypeptide can be prepared by mutations in the DNA. This may also be accomplished by one of several forms of mutagenesis and/or in directed evolution.

In some aspects, the changes encoded in the amino acid sequence will not substantially affect the function of the protein. Such variants will possess the desired pesticidal activity. However, it is understood that the ability of an IRDIG35563 polypeptide to confer pesticidal activity may be improved using such techniques upon the compositions of this disclosure.

In some embodiments, the translation initiator methionine of the IRDIG35563 polypeptide is cleaved off post translationally, for example by a methionine aminopeptidase in many cellular expression systems.

Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: nonpolar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

Classes of amino acids

| Class of Amino Acid | Examples of Amino Acids |
|---|---|
| Nonpolar Side Chains | Ala (A), Val (V), Leu (L), Ile (I), Pro (P), Met (M), Phe (F), Trp (W) |
| Uncharged Polar Side Chains | Gly (G), Ser (S), Thr (T), Cys (C), Tyr (Y), Asn (N), Gln (Q) |
| Acidic Side Chains | Asp (D), Glu (E) |
| Basic Side Chains | Lys (K), Arg (R), His (H) |
| Beta-branched Side Chains | Thr, Val, Ile |
| Aromatic Side Chains | Tyr, Phe, Trp, His |

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by inclusion of amino acid encoding sequences in the oligonucleotides utilized in the PCR amplification.

Alternatively, the protein sequences added can include entire protein-coding sequences, to generate protein fusions. Such fusion proteins are often used to (1) increase expression of a protein of interest (2) introduce a binding domain, enzymatic activity or epitope to facilitate either protein purification, protein detection or other experimental uses (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different IRDIG35563 polypeptide coding regions can be used to create a new IRDIG35563 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling include for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered IRDIG35563 polypeptides. Domains may be swapped between IRDIG35563 polypeptides resulting in further hybrid or chimeric toxins with improved insecticidal activity or target spectrum.

Pesticidal proteins of the present invention are encoded by a nucleotide sequence sufficiently identical to the nucleotide sequence of SEQ ID NO:1, or the pesticidal proteins are sufficiently identical to the amino acid sequence set forth in SEQ ID NO:2.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence. The percent identity between two sequences can be determined using techniques similar to those described below, with or without allowing gaps. In calculating percent identity, typically exact matches are counted. A gap, (a position in an alignment where a residue is present in one sequence but not in the other) is regarded as a position with non-identical residues.

The determination of percent identity between two sequences can be accomplished using a mathematical algorithm. A non-limiting example of a mathematical algorithm utilized for the comparison of two sequences is the algorithm incorporated into the BLASTN and BLASTX programs. Karlin and Altschul (1990) Proc. Nat'l. Acad. Sci. USA 87:2264, Altschul et al. (1990) *J. Mol. Bioi.* 215:403, and Karlin and Altschul (1993) Proc. Nat'l. Acad. Sci. USA 90:5873-5877. BLAST nucleotide searches can be performed with the BLASTN program, score=100, word length=12, to obtain nucleotide sequences homologous to pesticidal-like nucleic acid molecules of the invention. BLAST protein searches can be performed with the BLASTX program, score=50, word length=3, to obtain amino acid sequences homologous to pesticidal protein molecules of the invention. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™ GENEDOC™ (Karl Nicholas) allows assessment of amino acid (or DNA) similarity and identity between multiple proteins.

Another non-limiting example of a mathematical algorithm utilized for the comparison of sequences is the algorithm of Myers and Miller (1988) *CABIOS* 4(1):11-17. Such an algorithm is incorporated into the ALIGN program (version 2.0), which is part of the GCG Wisconsin Genetics Software Package, Version 10 (available from Accelrys, Inc., San Diego, Calif., USA). When utilizing the ALIGN program for comparing amino acid sequences, a PAM120 weight residue table, a gap length penalty of 12, and a gap penalty of 4 can be used. Unless otherwise stated, GAP Version 10, which uses the algorithm of Needleman and Wunsch (1970) *J Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

In another embodiment of the invention, protease cleavage sites may be engineered at desired locations to affect protein processing within the midgut of susceptible larvae of certain insect pests. These protease cleavage sites may be introduced by methods such as chemical gene synthesis or splice overlap PCR (Horton et al., 1989). Serine protease recognition sequences, for example, can optionally be inserted at specific sites in the Cry protein structure to affect protein processing at desired deletion points within the midgut of susceptible larvae. Serine proteases that can be exploited in such fashion include Lepidopteran midgut serine proteases such as trypsin or trypsin-like enzymes, chymotrypsin, elastase, etc. (Christeller et al., 1992). Further, deletion sites identified empirically by sequencing Cry protein digestion products generated with unfractionated larval midgut protease preparations or by binding to brush border membrane vesicles can be engineered to effect protein activation.

Lepidopteran and Coleopteran serine proteases such as trypsin, chymotrypsin and cathepsin G-like protease, Lepidopteran and Coleopteran cysteine proteases such as cathepsins (B-like, L-like, O-like, and K-like proteases) (Koiwa et al., (2000) and Bown et al., (2004)), Lepidopteran and Coleopteran metalloproteases such as ADAM10 (Ochoa-Campuzano et al., (2007)), and Lepidoperan and Coleopteran aspartic acid proteases such as cathepsins D-like and E-like, pepsin, plasmin, and chymosin may further be exploited by engineering appropriate recognition sequences at desired processing sites to affect Cry protein processing within the midgut of susceptible larvae of certain insect pests and perhaps also function to provide activity against non-susceptible insect pests.

IRDIG35563 variants can be produced by introduction or elimination of protease processing sites at appropriate positions in the coding sequence to allow, or eliminate, proteolytic cleavage of a larger variant protein by insect, plant, or microorganism proteases are within the scope of the invention. The end result of such manipulation is understood to be the generation of toxin fragment molecules having the same or better function and/or activity as the intact (full length) toxin protein.

In another embodiment, fusion proteins are provided that include within its amino acid sequence an amino acid sequence comprising an IRDIG35563 polypeptide of the disclosure. Polynucleotides encoding an IRDIG35563 polypeptide may be fused to signal sequences which will direct the localization of the IRDIG35563 polypeptide to particular compartments of a prokaryotic or eukaryotic cell and/or direct the secretion of the IRDIG35563 polypeptide of the embodiments from a prokaryotic or eukaryotic cell. For example, in *E. coli*, one may wish to direct the expression of the protein to the periplasmic space. Examples of signal sequences or proteins (or fragments thereof) to which the IRDIG35563 polypeptide may be fused to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IRDIG35563 polypeptide may be fused to the pelB pectate lyase signal sequence to increase the efficiency of expression and purification of such polypeptides in Gram-negative bacteria (see, U.S. Pat. Nos. 5,576,195 and 5,846,818). The fusion protein may be a plant plastid transit peptide/polypeptide fusions or an Apoplast transit peptides such as rice or barley alpha-amylase secretion signal. The plastid transit peptide is generally fused N-terminal to the polypeptide to be targeted (e.g., the fusion partner). In one embodiment, the fusion protein consists essentially of the plastid transit peptide and the IRDIG35563 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide if the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, because of specific intercellular conditions or the combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity if the transit peptide cleavage site remains accessible and the function of the second protein is not altered by the addition of these extra amino acids at its N-terminus. Precise cleavage site between the transit peptide and the second protein (with or without its initiator methionine) can be created using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29):15104-9. In some embodiments, the IRDIG35563 polypeptide is fused to a heterologous signal peptide or heterologous transit peptide.

Nucleic Acid Molecules, and Variants and Fragments Thereof.

Isolated or recombinant nucleic acid molecules comprising nucleic acid sequences encoding IRDIG35563 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences that encode IRDIG35563, its variants and truncations, may be synthesized and cloned into standard plasmid vectors by conventional means, or may be obtained by standard molecular biology manipulation of other constructs containing the nucleotide sequences. Unique restriction sites internal to an IRDIG35563 coding region may be identified and DNA fragments comprising the sequences between the restriction sites of the IRDIG35563 coding region may be synthesized, each such fragment encoding a specific deletion, insertion or other IRDIG35563 variation. The DNA fragments encoding the modified IRDIG35563 fragments may be joined to other IRDIG35563 coding region fragments or other Cry or VIP coding region fragments at appropriate restriction sites to obtain a coding region encoding the desired full-length IRDIG35563 protein, deleted or variant IRDIG35563 protein. For example, one may identify an appropriate restriction recognition site at the start of a first IRDIG35563 coding region, and a second restriction site internal to the IRDIG35563 coding region. Cleavage of this first IRDIG35563 coding region at these restriction sites would generate a DNA fragment comprising part of the first IRDIG35563 coding region. A second DNA fragment flanked by analogously-situated compatible restriction sites specific for another IRDIG35563 coding region may be used in combination with the first DNA restriction fragment to construct a variant.

In some embodiments, the nucleic acid molecule encoding an IRDIG35563 polypeptide is a polynucleotide having the sequence set forth in SEQ ID NO: 1, and variants, fragments and complements thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In some embodiments, the nucleic acid molecule encoding the IRDIG35563 polypeptide is a non-genomic nucleic acid sequence.

In some embodiments, the nucleic acid molecule encoding an IRDIG35563 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 1, wherein the encoded IRDIG35563 polypeptide has insecticidal activity.

In some embodiments, the IRDIG35563 polynucleotide encodes an IRDIG35563 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, and has at least one amino acid substitution, deletion, insertion or combination therefore, compared to the native sequence.

In some embodiments, the nucleic acid molecule encodes an IRDIG35563 polypeptide comprising an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2.

Bacterial genes quite often possess multiple methionine initiation codons in proximity to the start of the open reading frame. Often, translation initiation at one or more of these start codons will lead to generation of a functional protein. Start codons can be ATG codons. Certain bacteria such as *Bacillus* sp. also recognize the codon GTG as a start codon. On rare occasions, translation in bacterial systems can initiate at a TTG codon. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

The polynucleotide coding sequence can be modified to add a codon at the penultimate position following the methionine start codon to create a restriction enzyme site for recombinant cloning purposes and/or for expression purposes. In some embodiments, the IRDIG35563 polypeptide further comprises an alanine residue at the position after the translation initiator methionine.

Nucleic acid molecules that are fragments of these nucleic acid sequences encoding IRDIG35563 polypeptides are also encompassed by the embodiments. A fragment of a nucleic acid sequence may encode a biologically active portion of an IRDIG35563 polypeptide or it may be a fragment that can be used as a hybridization probe or PCR primer using methods disclosed below. Nucleic acid molecules that are fragments of a nucleic acid sequence that are contiguous or up to the number of nucleotides present in a full-length nucleic acid sequence disclosed herein, depending upon the intended use. Fragments of the nucleic acid sequences of the embodiments will encode protein fragments that retain the biological activity of the IRDIG35563 polypeptide and, hence, retain insecticidal activity. In some embodiments, the IRDIG35563 polypeptide retains at least about 10%, at least about 30%, at least about 50%, at least about 70%, 80%, 90%, 95% or higher of the insecticidal activity of the full-length IRDIG35563 polypeptide. In some embodiments, the insecticidal activity is against a Lepidopteran species. In some embodiments, the insecticidal activity is against one or more insect pests selected from BAW, SAW, FAW, CEW, TBW, SBL, VBC, and CBW.

In some embodiments, the nucleic acid encodes an IRDIG35563 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2. In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX module of the Vector NTI Program Suite (Invitrogen Corporation, Carlsbad, Calif.) with all default parameters.

The embodiments also encompass nucleic acid molecules encoding IRDIG35563 polypeptide variants. "Variants" of the IRDIG35563 polypeptide encoding nucleic acid sequences include those sequences that encode the IRDIG35563 polypeptides disclosed herein but that differ conservatively because of the degeneracy of the genetic code as well as those that are sufficiently identical as discussed above. Variant nucleic acid sequences also include synthetically derived nucleic acid sequences that have been generated, for example, by using site-directed mutagenesis but which still encode the IRDIG35563 polypeptides disclosed as discussed below.

The present disclosure provides isolated or recombinant polynucleotides that encode any of the IRDIG35563 polypeptides disclosed herein. Due to the degeneracy of the genetic code, a multitude of nucleotide sequences encoding IRDIG35563 polypeptides of the present disclosure exist.

Changes can be introduced by mutation of the nucleic acid sequences thereby leading to changes in the amino acid sequence of the encoded IRDIG35563 polypeptides, without compromising the functional activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made during the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J. Mol. Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene*, 164:49-53; Stemmer, (1995) *Science* 270: 1510; Stemmer, (1995) *Bio/Technology* 13:549-553; Stemmer, (1994) *Nature* 370: 389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundstrom, et al., (1985) *Nucl Acids Res* 13:3305-3316), double-strand break repair (Mandecki, (1986) *PNAS USA*, 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Development of Oligonucleotide Probes.

A further method for identifying the toxins and genes of the subject invention is through the use of oligonucleotide probes. These probes are detectable nucleotide sequences. These sequences may be rendered detectable by virtue of an appropriate radioactive label or may be made inherently fluorescent as described in, for example, U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Nucleic Acid Hybridization.

As is well known to those skilled in molecular biology, similarity of two nucleic acids can be characterized by their tendency to hybridize. As used herein the terms “stringent conditions” or “stringent hybridization conditions” are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984): $T_m$(° C.)=81.5° C.+16.6(log M)+0.41(% GC)—0.61(% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. Alternatively, the $T_m$ is described by the following formula (Beltz et al., 1983): $T_m$(° C.)=81.5° C.+16.6(log[Na+])+0.41(% GC)−0.61(% formamide)−600/L where [Na+] is the molarity of sodium ions, % GC is the percentage of guanosine and cytosine nucleotides in the DNA, % formamide is the percentage of formamide in the hybridization solution, and L is the length of the hybrid in base pairs. Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Hybridization with Nucleic Acid Probes Vol. 1 by P. Tijssen (1993, ISBN-10: 0444898840, ISBN-13: 9780444898845 Hardcover) and Ausubel et al. (1995). Also see Sambrook et al. (1989).

Anti-Toxin Antibodies.

Antibodies to the toxins disclosed herein, or fragments of these toxins, can be prepared using standard procedures well known in the art. Such antibodies are useful to detect the presence of IRDIG35563 toxins in plant tissues and a variety of other substances. Such antibodies and anti-sera are useful in various methods of detecting the claimed IRDIG35563 toxins of the invention, and variants or fragments thereof. It is well known that antibodies labeled with a reporting group can be used to identify the presence of antigens in a variety of milieus. Antibodies labeled with radioisotopes have been used in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the Bt insecticidal toxin of the present invention can be bound to an immobilizing substance such as a polystyrene well or particle and used in immunoassays to determine whether the Bt toxin is present in a test sample. Anti-IRDIG35563 antibodies are also used for isolating quantities of IRDIG35563 toxins from recombinant production systems or natural sources.

A kit for detecting the presence of an IRDIG35563 polypeptide or detecting the presence of a nucleotide sequence encoding an IRDIG35563 polypeptide in a sample is provided. In one embodiment, the kit provides antibody-based reagents for detecting the presence of an IRDIG35563 polypeptide in a tissue sample. In another embodiment, the kit provides labeled nucleic acid probes useful for detecting the presence of one or more polynucleotides encoding an IRDIG35563 polypeptide. The kit is provided along with appropriate reagents and controls for carrying out a detection method, as well as instructions for use of the kit.

Transgenic Expression of IRDIG35563.

The subject protein toxins can be “applied” or provided to contact the target insects in a variety of ways. For example, IRDIG35563 toxins can be used as plant-incorporated protectants in transgenic plants (produced by and present in the plant). Expression of the toxin genes can also achieve selectivity in specific tissues of the plants, such as the roots, leaves, etc. This can be accomplished via the use of tissue-specific promoters.

A preferred embodiment of the subject invention is the transformation of plants with genes encoding the subject insecticidal protein or its variants. The transformed plants are resistant to prolonged attack by an insect target pest by virtue of the presence of controlling amounts of the subject insecticidal protein or its variants in the cells of the transformed plant. By incorporating and expressing genetic material that encodes an IRDIG35563 toxin into the genome of a plant eaten by a particular insect pest, the adult or larvae will die after consuming the food plant. Numerous members of the monocotyledonous and dicotyledonous classifications have been transformed. Transgenic agronomic crops as well as fruits and vegetables are of commercial interest. Such crops include, but are not limited to, maize, rice, soybeans, canola, sunflower, alfalfa, sorghum, wheat, cotton, peanuts, tomatoes, potatoes, and the like. Numerous well known techniques exist for introducing foreign genetic material into monocot or dicot plant cells, and for obtaining fertile plants that stably maintain and express the introduced gene.

In one preferred embodiment, IRDIG35563 or a variant is delivered orally through a transgenic plant comprising a nucleic acid sequence that expresses a toxin of the present invention. The present invention provides a method of producing an insect-resistant transgenic plant, comprising introducing a nucleic acid molecule of the invention into the plant wherein the toxin is expressible in the transgenic plant in an effective amount to control an insect. In a non-limiting example, a basic cloning strategy may be to subclone full length or modified IRDIG35563 coding sequences into a plant expression plasmid at NcoI and Sac/restriction sites. The resulting plant expression cassettes containing the appropriate IRDIG35563 coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen, Carlsbad, Calif.) for example, may be used to recombine the full length and modified gene plant expression cassettes into a binary plant transformation plasmid if the Gateway® technology is utilized. It is convenient to employ a binary plant transformation vector that harbors a bacterial gene that confers resistance to the antibiotic spectinomycin when the plasmid is present in *E. coli* and *Agrobacterium* cells. It is also convenient to employ a binary vector plasmid that contains a plant-expressible selectable marker gene that is functional in the desired host plants. Examples of plant-expressible selectable marker genes include but are not limited to those that encode the aminoglycoside phosphotransferase gene (aphII) of transposon Tn5, which confers resistance to the antibiotics kanamycin, neomycin and G418, as well as those genes which code for resistance or tolerance to glyphosate; hygromycin; methotrexate; phosphinothricin (bialaphos), imidazolinones, sulfonylureas and triazolopyrimidine herbicides, such as chlorosulfuron, bromoxynil, dalapon and the like.

Alternatively, the plasmid structure of the binary plant transformation vector containing the IRDIG35563 gene insert is performed by restriction digest fingerprint mapping of plasmid DNA prepared from candidate *Agrobacterium* isolates by standard molecular biology methods well known to those skilled in the art of *Agrobacterium* manipulation.

The use of the term "nucleotide constructs" herein is not intended to limit the embodiments to nucleotide constructs comprising DNA. Nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IRDIG35563 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments.

As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments, the DNA construct comprises a polynucleotide encoding an IRDIG35563 polypeptide of the embodiments.

In some embodiments, the DNA construct comprises a polynucleotide encoding a fusion protein comprising an IRDIG35563 polypeptide of the embodiments.

In some embodiments, the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers including, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al, (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize usage for 28 genes from maize plants is listed in Table 4 of Murray, et al., supra. Methods for synthesizing plant-preferred genescan be found in Murray, et al., (1989) *Nucleic Acids Res.* 17:477-498, and Liu H et al. *Mol Bio Rep* 37:677-684, 2010, herein incorporated by reference. A *Zea* maize usage table can be also found at kazusa.or.jp//cgi-bin/show.cgi?species=4577, which can be accessed using the www prefix.

A *Glycine max* usage table can be found at kazusa.or.jp//cgi-bin/show.cgi?species=3847&aa=1&style=N, which can be accessed using the www prefix.

In some embodiments, the recombinant nucleic acid molecule encoding an IRDIG35563 polypeptide has maize optimized codons. In some embodiments, the recombinant nucleic acid molecule encoding an IRDIG35563 polypeptide has soy optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA, ed. Cech (Liss,* New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. *Plant Cell* 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research*, 78:249-264, 2003. Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *ZeaMays* ssRUBISCO, *Zea Mays*-beta-glucosidase, *Zea Mays*-Malate dehydrogenase, *Zea Mays* Thioredoxin M-type US Patent Application Publication 2012/0304336).

The IRDIG35563 polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

Several promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters include but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) Plant). 14(2): 247-257) and tetracycline-inducible and tetracycline-repressible promoters (see, for example, Gatz, et al., (1991) *Mol.*

Gen. Genet. 227:229-237 and U.S. Pat. Nos. 5,814,618 and 5,789,156), herein incorporated by reference.

Tissue-preferred promoters can be utilized to target IRDIG35563 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters can be found in Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, Plant Science (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Ciml (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608, 144; 5,604,121; 5,569,597; 5,466,785; 5,399,680; 5,268, 463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991)

Plant Mol. Biol. 16:807-820); streptomycin (Jones, et al., (1987) Mol. Gen. Genet. 210:86-91); spectinomycin (Bretagne-Sagnard, et al., (1996) Transgenic Res. 5:131-137); bleomycin (Hille, et al., (1990) Plant Mol. Biol. 7:171-176); sulfonamide (Guerineau, et al., (1990) Plant Mol. Biol. 15:127-136); bromoxynil (Stalker, et al., (1988) Science 242:419-423); glyphosate (Shaw, et al., (1986) Science 233:478-481 and U.S. patent application Ser. Nos. 10/004,357 and 10/427,692); phosphinothricin (DeBlock, et al., (1987) EMBO J. 6:2513-2518). See generally, Yarranton, (1992) Curr. Opin. Biotech. 3:506-511; Christopherson, et al., (1992) Proc. Natl. Acad. Sci. USA 89:6314-6318; Yao, et al., (1992) Cell 71:63-72; Reznikoff, (1992) Mol. Microbiol. 6:2419-2422; Barkley, et al., (1980) in The Operon, pp. 177-220; Hu, et al., (1987) Cell 48:555-566; Brown, et al., (1987) Cell 49:603-612; Figge, et al., (1988) Cell 52:713-722; Deuschle, et al., (1989) Proc. Natl. Acad. Sci. USA 86:5400-5404; Fuerst, et al., (1989) Proc. Natl. Acad. Sci. USA 86:2549-2553; Deuschle, et al., (1990) Science 248:480-483; Gossen, (1993) Ph.D. Thesis, University of Heidelberg; Reines, et al., (1993) Proc. Natl. Acad. Sci. USA 90:1917-1921; Labow, et al., (1990) Mol. Cell. Biol. 10:3343-3356; Zambretti, et al., (1992) Proc. Natl. Acad. Sci. USA 89:3952-3956; Baim, et al., (1991) Proc. Natl. Acad. Sci. USA 88:5072-5076; Wyborski, et al., (1991) Nucleic Acids Res. 19:4647-4653; Hillenand-Wissman, (1989) Topics Mol. Struc. Biol. 10:143-162; Degenkolb, et al., (1991) Antimicrob. Agents Chemother. 35:1591-1595; Kleinschnidt, et al., (1988) Biochemistry 27:1094-1104; Bonin, (1993) Ph.D. Thesis, University of Heidelberg; Gossen, et al., (1992) Proc. Natl. Acad. Sci. USA 89:5547-5551; Oliva, et al., (1992) Antimicrob. Agents Chemother. 36:913-919; Hlavka, et al., (1985) Handbook of Experimental Pharmacology, Vol. 78 (Springer-Verlag, Berlin) and Gill, et al., (1988) Nature 334:721-724. Such disclosures are herein incorporated by reference.

The above list of selectable marker genes is not meant to be limiting. Any selectable marker gene can be used in the embodiments.

Those skilled in the art of obtaining transformed plants via Agrobacterium-mediated transformation methods will understand that other Agrobacterium strains besides Z7075 may be used, and the choice of strain may depend upon the identity of the host plant species to be transformed.

The methods of the embodiments involve introducing a polypeptide or polynucleotide into a plant. "Introducing" as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants include but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) Biotechniques 4:320-334), electroporation (Riggs, et al., (1986) Proc. Natl. Acad. Sci. USA 83:5602-5606), Agrobacterium-mediated transformation (U.S. Pat. Nos. 5,563,055 and 5,981,840), direct gene transfer (Paszkowski, et al., (1984) EMBO J. 3:2717-2722) and ballistic particle acceleration (see, for example, U.S. Pat. Nos. 4,945,050; 5,879,918; 5,886,244 and 5,932,782; Tomes, et al., (1995) in Plant Cell, Tissue, and Organ Culture: Fundamental Methods, ed. Gamborg and Phillips, (Springer-Verlag, Berlin) and McCabe, et al., (1988) Biotechnology 6:923-926) and Led transformation (WO 00/28058). For potato transformation see, Tu, et al., (1998) Plant Molecular Biology 37:829-838 and Chong, et al., (2000) Transgenic Research 9:71-78. Additional transformation procedures can be found in Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); McCabe, et al., (1988) Bio/Technology 6:923-926 (soybean); Finer and McMullen, (1991) In Vitro Cell Dev. Biol. 27P:175-182 (soybean); Singh, et al., (1998) Theor. Appl. Genet. 96:319-324 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); U.S. Pat. Nos. 5,240,855; 5,322,783 and 5,324,646; Klein, et al., (1988) Plant Physiol. 91:440-444 (maize); Fromm, et al., (1990) Biotechnology 8:833-839 (maize); Hooykaas-Van Slogteren, et al., (1984) Nature (London) 311:763-764; U.S. Pat. No. 5,736,369 (cereals); Bytebier, et al., (1987) Proc. Natl. Acad. Sci. USA 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) Plant Cell Reports 9:415-418 and Kaeppler, et al., (1992) Theor. Appl. Genet. 84:560-566 (whisker-mediated transformation); D'Halluin, et al., (1992) Plant Cell 4:1495-1505 (electroporation); Li, et al., (1993) Plant Cell Reports 12:250-255 and Christou and Ford, (1995) Annals of Botany 75:407-413 (rice); Osjoda, et al., (1996) Nature Biotechnology 14:745-750 (maize via Agrobacterium tumefaciens); all of which are herein incorporated by reference.

In specific embodiments, the sequences of the embodiments can be provided to a plant using a variety of transient transformation methods. Such transient transformation methods include, but are not limited to, the introduction of the IRDIG35563 polynucleotide or variants and fragments thereof directly into the plant or the introduction of the IRDIG35563 polypeptide transcript into the plant. Such methods include, for example, microinjection or particle bombardment. See, for example, Crossway, et al., (1986) Mol Gen. Genet. 202:179-185; Nomura, et al., (1986) Plant Sci. 44:53-58; Hepler, et al., (1994) Proc. Natl. Acad. Sci. 91:2176-2180 and Hush, et al., (1994) The Journal of Cell Science 107:775-784, all of which are herein incorporated by reference. Alternatively, the IRDIG35563 polynucleotide can be transiently transformed into the plant using techniques in viral vector system and the precipitation of the polynucleotide in a manner that precludes subsequent release of the DNA. Thus, transcription from the particlebound DNA can occur, but the frequency with which it is released to become integrated into the genome is greatly reduced. Such methods include the use of particles coated with polyethylimine (PEI; Sigma #P3143).

Methods for the targeted insertion of a polynucleotide at a specific location in the plant genome include the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation including plant transformation vectors that are comprised of more than one contiguous DNA segment. These vectors are often referred to as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one can identify and proliferate the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the disclosed embodiments include IRDIG35563 polypeptides that are initially synthesized as part of a viral polyprotein, which later may be processed by proteolysis in vivo or in vitro to produce the desired IRDIG35563 polypeptide end product. It is also recognized that such a viral polyprotein, comprising at least a portion of the amino acid sequence of an IRDIG35563 of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931; herein incorporated by reference.

Methods for transformation of chloroplasts can be found for example in Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus* casica), guava (*Psidium guajava*), mango (*Mangifera indica*), olive (*Olea europaea*), papaya (*Carica papaya*), cashew (*Anacardium* occidentals), macadamia (Macadamia integrifolia), almond (*Prunus* amygdalus), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (Hibiscus rosasanensis), roses (*Rosa* spp.), tulips (*Tulipa* spp.), daffodils (*Narcissus* spp.), petunias (*Petunia hybrida*), carnation (*Dianthus* caryophyllus), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinelha distans*); western wheatgrass (*Agropyron smithii*); Bermuda grass (*Cynodon* spp.); St. Augustine grass (*Stenotaphrum secundatum*); *Zoysia* grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore Paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Plant Transformation. Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that can be found in Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IRDIG35563 polypeptide.

Insect Bioassays of transgenic *Arabidopsis*. Transgenic *Arabidopsis* lines expressing modified IRDIG35563 proteins can be used to demonstrate activity against sensitive insect species in artificial diet overlay assays. Protein extracted from transgenic and non-transgenic *Arabidopsis* lines may be quantified by appropriate methods and sample volumes adjusted to normalize protein concentration. Bioassays are then conducted on artificial diet as described below. Non-transgenic *Arabidopsis* and/or buffer and water should be included in assays as background check treatments.

Bioassay of transgenic maize. Bioactivity of the IRDIG35563 toxins and variants produced in plant cells also may be demonstrated by conventional bioassay methods (see, for example Huang et al., 2006). Efficacy may be tested by feeding various plant tissues or tissue pieces derived from a plant producing an IRDIG35563 toxin to target insects in a controlled feeding environment. Alternatively, protein extracts may be prepared from various plant tissues derived from a plant producing the IRDIG35563 toxin and incorporate the extracted proteins in an artificial diet bioassay. It is to be understood that the results of such feeding assays are to be compared to similarly conducted bioassays that employ appropriate control tissues from host plants that do not produce the IRDIG35563 protein or variants, or to other control samples.

Methods to Introduce Genome Editing Technologies into Plants. In some embodiments, the disclosed IRDIG35563 polynucleotide compositions can be introduced into the genome of a plant using genome editing technologies, or previously introduced IRDIG35563 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IRDIG35563 polynucleotide has previously been introduced into a genome, genome editing technologies may be used to alter or modify the introduced polynucleotide sequence. Site specific modifications that can be introduced into the disclosed IRDIG35563 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IRDIG35563 polynucleotide compositions disclosed herein within the genome of a plant, to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plants.

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, the polynucleotides encoding the IRDIG35563 polypeptide disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including, but not limited to: insecticidal proteins from *Pseudomonas* sp. such as PSEEN3174 (Monalysin; (2011) *PLoS Pathogens* 7:1-13); from *Pseudomonas protegens* strain CHA0 and Pf-5 (previously *fluorescens*) (Pechy-Tarr, (2008) *Environmental Microbiology* 10:2368-2386; GenBank Accession No. EU400157); from *Pseudomonas taiwanensis* (Liu, et al., (2010) *J. Agric. Food Chem.,* 58:12343-12349) and from *Pseudomonas pseudoalcaligenes* (Zhang, et al., (2009) *Annals of Microbiology* 59:45-50 and Li, et al., (2007) Plant Cell Tiss. Organ Cult. 89:159-168); insecticidal proteins from *Photorhabdus* sp. and *Xenorhabdus* sp. (Hinchliffe, et al., (2010) The Open Toxicology Journal, 3:101-118 and Morgan, et al., (2001) Applied and Envir. Micro. 67:2062-2069); U.S. Pat. Nos. 6,048,838, and 6,379,946; a PIP-1 polypeptide of U.S. Pat. No. 9,688,730; an AfIP-1A and/or AfIP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of U.S. Ser. No. 62/521,084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of US Serial Number U.S. 62/508,514; and δ-endotoxins including, but not limited to a Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin polypeptides and the *B. thuringiensis* cytolytic cyt1 and cyt2 genes. Members of these classes of *B. thuringiensis* insecticidal proteins can be found in Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275, 7,858,849, and 8,878,007; a Cry1Ac mutant of U.S. Pat. No. 9,512,187; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476, 226; Cry1B of U.S. patent application Ser. No. 10/525,318, US Patent Application Publication Number US20160194364, and U.S. Pat. Nos. 9,404,121 and 8,772, 577; Cry1B variants of PCT Publication Number WO2016/61197 and Serial Number PCT/US17/27160; Cry1C of U.S. Pat. No. 6,033,874; Cry1D protein of US20170233759; a Cry1E protein of PCT Serial Number PCT/US17/53178; a Cry1F protein of U.S. Pat. Nos. 5,188,960 and 6,218,188; Cry1A/F chimeras of U.S. Pat. Nos. 7,070,982; 6,962,705 and 6,713,063; a Cry1 protein of PCT Publication number WO 2017/0233759; a Cry1J variant of US Publication US20170240603; a Cry2 protein such as Cry2Ab protein of U.S. Pat. No. 7,064,249 and Cry2A.127 protein of U.S. Pat. No. 7,208,474; a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476, 781, 7,105,332, 7,339,092, 7,378,499, 7,462,760, and 9,593, 345; a Cry9 protein such as such as members of the Cry9A, Cry9B, Cry9C, Cry9D, Cry9E and Cry9F families including the Cry9 protein of U.S. Pat. Nos. 9,000,261 and 8,802,933, and US Serial Number WO 2017/132188; a Cry15 protein of Naimov, et al., (2008) *Applied and Environmental Microbiology*, 74:7145-7151; a Cry14 protein of U.S. Pat. No. 8,933,299; a Cry22, a Cry34Ab1 protein of U.S. Pat. Nos. 6,127,180, 6,624,145 and 6,340,593; a truncated Cry34 protein of U.S. Pat. No. 8,816,157; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein of U.S. Pat. No. 9,403,881, a Cry 51 protein, a Cry binary toxin; a TIC901 or related toxin; TIC807 of US Patent Application Publication Number 2008/0295207; TIC853 of US Patent U.S. Pat. No. 8,513,493; ET29, ET37, TIC809, TIC810, TIC812, TIC127, TIC128 of PCT US 2006/033867; engineered Hemipteran toxic proteins of US Patent Application Publication Number US20160150795, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI046, AXMI048, AXMI050, AXMI051, AXMI052, AXMI053, AXMI054, AXMI055, AXMI056, AXMI057, AXMI058, AXMI059, AXMI060, AXMI061, AXMI067, AXMI069, AXMI071, AXMI072, AXMI073, AXMI074, AXMI075, AXMI087, AXMI088, AXMI093, AXMI070, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI125, AXMI126, AXMI127, AXMI129, AXMI151, AXMI161, AXMI164, AXMI183, AXMI132, AXMI137, AXMI138 of US Patent U.S. Pat. Nos. 8,461,421 and 8,461,422; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, dsAXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent U.S. Pat. No. 8,461,421; AXMI192 of U.S. Pat. No. 8,461,415; AXMI281 of US Patent Application Publication Number US20160177332; AXMI422 of U.S. Pat. No. 8,252,872; cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The Cry proteins MP032, MP049, MP051, MP066, MP068, MP070, MP091S, MP109S, MP114, MP121, MP134S, MP183S, MP185S, MP186S, MP195S, MP197S, MP208S, MP209S, MP212S, MP214S, MP217S, MP222S, MP234S, MP235S, MP237S, MP242S, MP243, MP248, MP249S, MP251M, MP252S, MP253, MP259S, MP287S, MP288S, MP295S, MP296S, MP297S, MP300S, MP304S, MP306S, MP310S, MP312S, MP314S, MP319S, MP325S, MP326S, MP327S, MP328S, MP334S, MP337S, MP342S, MP349S, MP356S, MP359S, MP360S, MP437S, MP451S, MP452S, MP466S, MP468S, MP476S, MP482S, MP522S, MP529S, MP548S, MP552S, MP562S, MP564S, MP566S, MP567S, MP569S, MP573S, MP574S, MP575S, MP581S, MP590, MP594S, MP596S, MP597, MP599S, MP600S, MP601S, MP602S, MP604S, MP626S, MP629S, MP630S, MP631S, MP632S, MP633S, MP634S, MP635S, MP639S, MP640S, MP644S, MP649S, MP651S, MP652S, MP653S, MP661S, MP666S, MP672S, MP696S, MP704S, MP724S, MP729S, MP739S, MP755S, MP773S, MP799S, MP800S, MP801S, MP802S, MP803S, MP805S, MP809S, MP815S, MP828S, MP831S, MP844S, MP852, MP865S, MP879S, MP887S, MP891S, MP896S, MP898S, MP935S, MP968, MP989, MP993, MP997, MP1049, MP1066, MP1067, MP1080, MP1081, MP1200, MP1206, MP1233, and MP1311 of U.S. Ser. No. 62/607,372. The insecticidal activity of Cry proteins can be found for example in van Frannkenhuyzen, (2009) J. Invert. Path. 101:1-16). The use of Cry proteins as transgenic plant traits art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) Plant Biotech Journal 9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1DA & Cry1BE (US2012/0331590); Cry1DA & Cry1Fa (US2012/0331589); Cry1AB & Cry1BE (US2012/0324606); Cry1Fa & Cry2Aa and Cry1I & Cry1E (US2012/0324605); Cry34Ab/35Ab & Cry6Aa (US20130167269); Cry34Ab/VCry35Ab & Cry3Aa (US20130167268); Cry1Da & Cry1Ca (U.S. Pat. No. 9,796, 982); Cry3Aa & Cry6Aa (U.S. Pat. No. 9,798,963); and Cry3A & Cry1Ab or Vip3Aa (U.S. Pat. No. 9,045,766). Pesticidal proteins also include insecticidal lipases including lipid acyl hydrolases of U.S. Pat. No. 7,491,869, and cholesterol oxidases such as from *Streptomyces* (Purcell et al. (1993) Biochem Biophys Res Commun 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins can be found at lifesci.sussex.ac.uk/home/Neil_Crickmore/Bt/vip.html, which can be accessed on the world-wide web using the "www" prefix. Pesticidal proteins also include Cyt proteins including Cyt1A variants of PCT Serial Number PCT/US2017/000510; Pesticidal proteins also include toxin complex (TC) proteins, obtainable from organisms such as *Xenorhabdus, Photorhabdus* and *Paenibacillus* (see, U.S. Pat. Nos. 7,491,698 and 8,084, 418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087, 810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant* 2:367.

(N) A polynucleotide encoding a developmental-arrestive protein produced in nature by a plant. For example, Logemann, et al., (1992) Bio/Technology 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) Current Biology 5(2), Pieterse and Van Loon, (2004) Curr. Opin. Plant Bio. 7(4):456-64 and Somssich, (2003) Cell 113(7):815-6.

(P) Antifungal genes (Cornelissen and Melchers, (1993) Pl. Physiol. 101:709-712 and Parijs, et al., (1991) Planta 183:258-264 and Bushnell, et al., (1998) Can. J. of Plant Path. 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) Planta 204:472-479, Williamson, (1999) Curr Opin Plant Bio. 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion.

2. Transgenes that Confer Resistance to an Herbicide, for Example:

(A) A polynucleotide encoding resistance to an herbicide that inhibits the growing point or meristem, such as an imidazolinone or a sulfonylurea. Exemplary genes in this category code for mutant ALS and AHAS enzyme as described, for example, by Lee, et al., (1988) EMBO J. 7:1241 and Miki, et al., (1990) Theor. Appl. Genet. 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT), *Streptomyces coelicolor* (A3) selectable marker (DSM-2), and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876; 6,040,497; 5,804,425; 5,633,435; 5,145,783; 4,971,908; 5,312,910; 5,188,642; 5,094,945, 4,940,835; 5,866,775; 6,225,114; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) Bio/Technology 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 and 5,879,903, which are incorporated herein by reference for this purpose. US 2011/0107455 discloses the DSM-2 gene and gene product sequences as well as their use in glufosinate herbicide-resistant plants. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) Theor. Appl. Genet. 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) Biochem. J. 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) Mol Gen Genet. 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,831 and 5,767, 373 and International Publication WO 2001/12825.

(F) The aad-1 gene (originally from Sphingobium *herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from Delftia *acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtI) described in Misawa, et al., (1993) *Plant J.* 4:833-840 and in Misawa, et al., (1994) *Plant J.* 6:481-489 for norflurazon tolerance.

3. Transgenes that confer or contribute to an altered grain characteristic;

4. Genes that control male sterility;

5. Genes that create a site for site specific DNA integration;

6. Genes that affect abiotic stress resistance;

7. Genes that confer increased yield; and/or

8. Genes that confer plant digestibility.

9. Gene silencing. In some embodiments, the stacked trait may be in the form of silencing of one or more polynucleotides of interest resulting in suppression of one or more target pest polypeptides. In some embodiments, the silencing is achieved using a suppression DNA construct.

In some embodiments, one or more polynucleotide encoding the IRDIG35563 polypeptides or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including Western corn rootworm to control insect infestation. Furthermore, PCT Publication WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publications 2014/0275208 and US2015/0257389 describe polynucleotide silencing elements targeting RyanR and PAT3. PCT Patent Application publication WO2016/138106 describes polynucleotide silencing elements targeting coatomer alpha or gamma. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubulin Homologous Sequence.

Use in Pesticidal Control. General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected to be capable of successfully competing in the particular environment with the wild-type microorganisms, provide for stable maintenance and expression of the gene expressing the IRDIG35563 polypeptide and desirably provide for improved protection of the pesticide from environmental degradation and inactivation.

Alternatively, the IRDIG35563 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IRDIG35563 polypeptides may then be formulated in accordance with conventional techniques for application to the environment hosting a target pest, e.g., soil, water, and foliage of plants. See, for example EPA 0192319, and the references cited therein.

Spray-on applications are another example and are also known in the art. The subject proteins can be appropriately formulated for the desired end use, and then sprayed (or otherwise applied) onto the plant or around the plant or to the vicinity of the plant to be protected before an infestation is discovered, after target insects are discovered, both before and after, and the like. Bait granules, for example, can also be used and are known in the art.

Pesticidal Compositions.

In some embodiments, the active ingredients can be applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants can be employed in the formulation. Suitable carriers and adjuvants can be solid or liquid and correspond to the substances ordinarily employed in formulation technology, e.g., natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient or an agrochemical composition that contains at least one of the IRDIG35563 polypeptide produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in each area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that can bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or another buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides.

Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus* thuriengiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrasulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments, the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments, the insecticide is Esfenvalerate, Chlorantraniliprole, Methomyl, Indoxacarb, Oxamyl or combinations thereof.

Pesticidal and Insecticidal Activity.

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hubner (beet armyworm); *S. litura* Fabricius (tobacco cutworm, cluster caterpillar); *Mamestra configurata* Walker (bertha armyworm); *M. brassicae* Linnaeus (cabbage moth); *Agrotis Ipsilon* Hufnagel (black cutworm); *A. orthogonia* Morrison (western cutworm); *A. subterranea* Fabricius (granulate cutworm); *Alabama argillacea* Hubner (cotton leaf worm); *Trichoplusia ni* Hubner (cabbage looper); *Pseudoplusia includens* Walker (soybean looper); *Anticarsia gemmatalis* Hubner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hubner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms, and skeletonizers from the family Pyralidae *Ostrinia nubilalis* Hubner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hubner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hubner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hubner (Indian meal moth); *Scirpophaga incertulas* Walker (yellow stem borer); *Udea rubigalis* Guenee (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rosslerstamm (summer fruit tortrix moth); *Cochylis hospes* Walsingham (banded sunflower moth); *Cydia latiferreana* Walsingham (filberworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hubner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; and *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Meneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hubner (elm spanworm); *Erannis tiliaria* Harris (linden looper); *Euproctis chrysorrhoea* Linnaeus (browntail moth); *Harrisina americana* Guérin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barber*/Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *Colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Gain (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *Phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); Pemphigus spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stal (rice leafhopper); *Nilaparvata lugens* Stal (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Kerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *Psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schiffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug);

*Lygus lineolaris* Palisot de Beauvois (tarnished plant bug); *L. Hesperus* Knight (Western tarnished plant bug); *L. pratensis* Linnaeus (common meadow bug); *L. ruguhpennis* Poppius (European tarnished plant bug); Lygocoris pabulinus Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hubner.

Methods for measuring pesticidal activity include for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment.

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides.

These compounds are typically formulated together with further carriers, surfactants or application-promoting adjuvants employed in the formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, trichoderma, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc.

Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for killing an insect pest and controlling an insect population. In some embodiments, methods are provided for killing an insect pest, comprising contacting the insect pest, either simultaneously or sequentially, with an insecticidally-effective amount of a recombinant IRDIG35563 polypeptide of the disclosure. In some embodiments, methods are provided for killing an insect pest, comprising contacting the insect pest with an insecticidally-effective amount of a recombinant pesticidal protein of SEQ ID NO: 2 or a variant thereof.

In some embodiments, methods are provided for controlling an insect pest population, comprising contacting the insect pest population, either simultaneously or sequentially, with an insecticidally-effective amount of a recombinant IRDIG35563 polypeptide of the disclosure. In some embodiments, methods are provided for controlling an insect pest population, comprising contacting the insect pest population with an insecticidally-effective amount of a recombinant IRDIG35563 polypeptide of SEQ ID NO: 2 or a variant thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments, methods are provided for controlling an insect pest population resistant to a pesticidal protein, comprising contacting the insect pest population, either simultaneously or sequentially, with an insecticidally-effective amount of a recombinant IRDIG35563 polypeptide of the disclosure. In some embodiments, methods are provided for controlling an insect pest population resistant to a pesticidal protein, comprising contacting the insect pest population with an insecticidally-effective amount of a recombinant IRDIG35563 polypeptide of SEQ ID NO: 2 or a variant thereof.

In some embodiments, methods are provided for protecting a plant from an insect pest, comprising expressing in the plant or cell thereof at least one recombinant polynucleotide encoding an IRDIG35563 polypeptide. In some embodiments, methods are provided for protecting a plant from an insect pest, comprising expressing in the plant or cell thereof a recombinant polynucleotide encoding IRDIG35563 polypeptide of SEQ ID NO: 2 or variants thereof.

Insect resistance management (IRM) strategies. Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments, the IRDIG35563 polypeptides of the disclosure are useful as an insect resistance management strategy in combination (i.e., pyramided) with other pesticidal proteins include but are not limited to Bt toxins, Xenorhabdus sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments, the methods of controlling Lepidoptera and/or Coleoptera insect infestation in a transgenic plant and promoting insect resistance management comprises the presentation of at least one of the IRDIG35563 polypeptide insecticidal proteins to insects in the order Lepidoptera and/or Coleoptera.

In some embodiments, the methods of controlling Lepidoptera and/or Coleoptera insect infestation in a transgenic plant and promoting insect resistance management comprises the presentation of at least one of the IRDIG35563 polypeptides of SEQ ID NO: 2, or variants thereof, insecticidal to insects in the order Lepidoptera and/or Coleoptera.

In some embodiments, the methods of controlling Lepidoptera and/or Coleoptera insect infestation in a transgenic plant and promoting insect resistance management comprise expressing in the transgenic plant an IRDIG35563 polypeptide and a Cry protein or other insecticidal protein to insects in the order Lepidoptera and/or Coleoptera having different modes of action.

In some embodiments, the methods, of controlling Lepidoptera and/or Coleoptera insect infestation in a transgenic plant and promoting insect resistance management, comprise expression in the transgenic plant an IRDIG35563 polypeptide of SEQ ID NO: 2 or variants thereof and a Cry protein or other insecticidal protein to insects in the order Lepidoptera and/or Coleoptera, where the IRDIG35563 polypeptide and Cry protein have different modes of action.

Also provided are methods of reducing likelihood of emergence of Lepidoptera and/or Coleoptera insect resistance to transgenic plants expressing in the plants insecticidal proteins to control the insect species, comprising expression of an IRDIG35563 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IRDIG35563 polypeptide and a Cry protein. Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IRDIG35563 polypeptide of SEQ ID NO: 2 or variants thereof and a Cry protein or other insecticidally active protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IRDIG35563 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IRDIG35563 polypeptide of SEQ ID NO: 2, or variant thereof does not compete with binding sites for Cry proteins in such insects.

Methods for increasing plant yield. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing an IRDIG35563 polypeptide disclosed herein. Expression of the IRDIG35563 polypeptide results in a reduced ability of a pest to infest or feed on the plant, thus improving plant yield.

Methods of processing. Further provided are methods of processing a plant, plant part or seed to obtain a food or feed product from a plant, plant part or seed comprising an IRDIG35563 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding an IRDIG35563 polypeptide which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds.

When an insect comes into contact and ingests an effective amount of toxin delivered via transgenic plant expression, formulated protein composition(s), sprayable protein composition(s), a bait matrix or other delivery system, the results are typically death of the insect, or the insects do not feed upon the source which makes the toxins available to the insects.

With suitable microbial hosts, e.g. *Pseudomonas*, the microbes can be applied to the environment of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

EXAMPLES

Example 1

Construction of expression plasmids encoding IRDIG35563 insecticidal toxin and expression in bacterial hosts. Standard cloning methods were used in the construction of *Pseudomonas fluorescens* (Pf) expression plasmids engineered to produce IRDIG35563 proteins encoded by plant-optimized coding regions. Restriction endonucleases and T4 DNA Ligase were obtained from New England BioLabs (NEB; Ipswich, Mass.) for restriction digestion and DNA ligation, respectively. Plasmid preparations were performed using the NucleoSpin® Plasmid Kit (Macherey-Nagel Inc, Bethlehem, Pa.) following the instructions of the suppliers for low-copy plasmid purification. DNA fragments were purified using a QIAquick® Gel Extraction Kit (Qiagen, Venio, Limburg) after agarose Tris-acetate gel electrophoresis.

The basic cloning strategy entailed subcloning the IRDIG35563 toxin coding sequence (CDS) (SEQ ID NO:1) into pDOW1169 at the SpeI and SalI restriction sites, whereby it is placed under the expression control of the Ptac promoter and the rrnBT1T2 terminator from plasmid pKK223-3 (PL Pharmacia, Milwaukee, Wis.). pDOW1169 is a medium copy plasmid with the RSF1010 origin of replication, a pyrF gene, and a ribosome binding site preceding the restriction enzyme recognition sites into which DNA fragments containing protein coding regions may be introduced, (US Application 20080193974). The expression plasmid, designated pDOW1169, was transformed by electroporation into DC454 (a near wild-type *P. fluorescens* strain having mutations deltapyrF and lsc:lacI$^{QI}$), or its derivatives, recovered in SOC-Soy hydrolysate medium, and plated on selective medium (M9 glucose agar lacking uracil, Sambrook et al., supra). Details of the microbiological manipulations are available in Squires et al., (2004), US Patent Application 20060008877, US Patent Application 20080193974, and US Patent Application 20080058262, incorporated herein by reference. Colonies were first screened by restriction digestion of miniprep plasmid DNA. Plasmid DNA of selected clones containing IRDIG35563 toxin were digested with four restriction enzymes and sequence verified to further validate presence of the insert.

Example 2

Growth and Expression Analysis in Shake Flasks. Production of IRDIG35563 toxin for characterization and insect bioassay was accomplished by shake-flask-grown *P. fluorescens* strains harboring expression constructs (pDOW1169). A glycerol stock of IRDIG35563 culture (0.5 mL) was inoculated into 50 mL of defined production medium with 9.5% glycerol (Teknova Catalog No. 3D7426, Hollister, Calif.). Expression of the IRDIG35563 toxin gene via the Ptac promoter was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described US Patent Application 20060008877.

Example 3

*Agrobacterium* Transformation.

Standard cloning methods were used in the construction of binary plant transformation and expression plasmids. Restriction endonucleases and T4 DNA Ligase were obtained from New England Biolabs. Plasmid preparations were performed using the NucleoSpin® Plasmid Preparation kit or the NucleoBond® AX Xtra Midi kit (both from Macherey-Nagel, Duren, Germany), following the instructions of the manufacturers. DNA fragments were purified using the QIAquick® PCR Purification Kit or the QIAEX IT® Gel Extraction Kit (both from Qiagen Venio, Limburg) after gel isolation.

Electro-competent cells of *Agrobacterium tumefaciens* strain Z7075 (a streptomycin-resistant derivative of Z707; Hepburn et al., 1985) were prepared and transformed using electroporation (Weigel and Glazebrook, 2002). After electroporation, 1 mL of Yeast Extract Peptone (YEP) broth (10 gm/L yeast extract, 10 gm/L peptone, and 5 gm/L NaCl) was added to the cuvette and the cell-YEP suspension was transferred to a 15 mL culture tube for incubation at 28° C. in a water bath with constant agitation for 4 hours. The cells were plated on YEP plus agar (25 gm/L) with spectinomycin (200 μg/mL) and streptomycin (250 μg/mL) and the plates were incubated for 2-4 days at 28° C. Well separated single colonies were selected and streaked onto fresh YEP+agar plates with spectinomycin and streptomycin as described above, and incubated at 28° C. for 1-3 days.

The presence of the IRDIG35563 gene insert in the binary plant transformation vector was performed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before was extracted using Qiagen (Venlo, Limburg, Netherlands) Spin® Mini Preps, performed per manufacturer's instructions. Plasmid DNA from the binary vector used in the *Agrobacterium* electroporation transformation was included as a control. The PCR reaction was completed using Taq DNA polymerase from Invitrogen (Carlsbad, Calif.) per manufacturer's instructions at 0.5× concentrations. PCR reactions were carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction was maintained at 4° C. after cycling. The amplification products were analyzed by agarose gel electrophoresis (e.g. 0.7% to 1% agarose, w/v) and visualized by ethidium bromide staining. A colony was selected whose PCR product was identical to the plasmid control.

Example 4

IRDIG35563 Purification.

Harvested Pf cells containing IRDIG35563 were sonicated in lysis buffer consisting of 50 mM Tris (pH 8.0), 1 M NaCl, 10% glycerol and 2 mM EDTA with 50 μL of Protease Inhibitor Cocktail (Sigma-Aldrich, St. Louis, Mo.) per 25 mL buffer. The extract was centrifuged at 20,000×g for 40 minutes. The soluble protein in the supernatant was precipitated with 50% ammonium sulfate and centrifuged at 20,000×g for 30 minutes. The pellet was resuspended in 50 mM Tris (pH 8.0) and centrifuged at 20,000×g for 20 minutes to pellet any soluble material. The supernatant containing IRDIG35563 was purified by anion exchange chromatography using a HiTrap™ Q HP 5 mL column with an AKTA Purifier chromatography system (GE Healthcare, UK). The column was equilibrated in 50 mM Tris (pH 8.0), and proteins were eluted with a stepwise gradient to 1 M NaCl. Protein-containing fractions were combined and concentrated using Amicon® Ultra-15 Centrifugal Filter Devices with a 30K MWCO (EMD Millipore, Burlington, Mass.). The IRDIG35563 protein sample was dialyzed overnight against 50 mM Tris (pH 8.), and total protein concentrations were measured with the NanoDrop 2000C Spectrophotometer (Thermo Scientific, Waltham, Mass.), using the A280 method.

Example 5

Gel Electrophoresis.

SDS-PAGE analysis was performed using NuPAGE® Novex® 4-12% Bis-Tris Protein Gels (Thermo Scientific, Waltham, Mass.). Proteins were diluted 4× in NuPAGE® LDS Sample Buffer (Thermo Scientific, Waltham, Mass.) containing 100 mM TCEP prior to loading onto the gel. Ten µL of Novex® Sharp Pre-stained Protein Standard was loaded onto one lane of each gel. Gels were run in NuPAGE® MES SDS Running Buffer according to the manufacturer's recommendations and stained with SimplyBlue™ SafeStain (Thermo Scientific, Waltham, Mass.), then destained in water and imaged on a flatbed scanner. Final protein preparation showed a single band of protein migrating at an apparent molecular weight of about 88 kDa.

Example 6

Sample Preparation and Bioassays.

Purified preparations of IRDIG35563 were diluted appropriately in 50 mM Tris, pH 8, and all bioassays contained a control treatment consisting of this buffer, which served as a background check for mortality and/or growth inhibition. Protein concentrations in bioassay buffer were estimated with the NanoDrop 2000C Spectrophotometer (Thermo Scientific, Waltham, Mass.), using the A280 method.

Purified proteins were tested for insecticidal activity in bioassays conducted with 1-2 day old neonate Lepidopteran larvae on artificial insect diet. Larvae of BAW, SAW, FAW, rFAW, CEW, TBW, SBL, VBC, and CBW were hatched from eggs obtained from a colony maintained by a commercial insectary (Benzon Research Inc., Carlisle, Pa.). Larvae of rFAW were hatched from eggs harvested from proprietary colonies (Dow AgroSciences LLC, Indianapolis, Ind.).

The bioassays were conducted in 128-well plastic trays specifically designed for insect bioassays (C-D International, Pitman, N.J.). Each well contained 2.0 mL of Multi-species Lepidoptera diet (Southland Products, Lake Village, Ark.). A 40 µL aliquot of protein sample was delivered by pipette onto the 2.0 cm$^2$ diet surface of each well (20 µL/cm$^2$). Diet concentrations were calculated as the amount (ng) of IRDIG35563 protein per square centimeter (cm$^2$) of surface area in the well. A 9 dose concentration range was used from 9,000 to 3 ng/cm$^2$ with 16 larvae tested per dose. *Helicoverpa armigera* bioassays used 7 different concentrations of purified protoxins, with a control of only buffer. Mortality and arrest were assessed after 7 days at 25° C. with 16:8 light:dark conditions. The treated trays were held in a fume hood until the liquid on the diet surface had evaporated or was absorbed into the diet.

Within 24-48 hours of eclosion, individual larvae were picked up with a moistened camel hair brush and deposited on the treated diet, one larva per well. The infested wells were then sealed with adhesive sheets of clear plastic and vented to allow gas exchange (C-D International, Pitman, N.J.). Bioassay trays were held under controlled environmental conditions (28° C., ~60% Relative Humidity, 16:8 [Light:Dark]) for 5 days, after which the total number of insects exposed to each protein sample, the number of dead insects, and the weight of surviving insects were recorded.

The GI$_{50}$ was determined to be the concentration of IRDIG35563 protein in the diet at which the GI value was 50%. The 50% lethal concentration (LC$_{50}$) was recorded as the concentration of IRDIG35563 protein in the diet at which 50% of test insects were killed. Growth inhibition concentration-response curves were determined by using a nonlinear logistic 3-parameter through JMP Pro, version 9.0.3, software (SAS Institute Inc., Cary, N.C.). Lethal concentration-response curve were analyzed by Probit analyses (Finney, 1971) of the pooled mortality data and were conducted using POLO-PC (LeOra Software). Table 2 shows the efficacy of purified IRDIG35563 against multiple insect species tested on artificial diet-overlay bioassay (ng/cm$^2$).

TABLE 2

| Target Insect | N | % mortality (3000 ng/cm$^2$) | Practical mortality (3000 ng/cm$^2$) |
|---|---|---|---|
| BAW | 16 | 100.0 | 100.0 |
| CBW | 16 | 100.0 | 100.0 |
| CEW | 46 | 21.7 | 65.2 |
| ECB | 16 | 6.3 | 12.5 |
| FAW | 32 | 93.8 | 100 |
| rFAW (Cry1F resistant) | 32 | 87.5 | 100 |
| SAW | 32 | 100.0 | 100.0 |
| SBL | 32 | 40.6 | 50.0 |
| TBW | 16 | 37.5 | 50.0 |
| VBC | 16 | 62.5 | 100.0 |

Example 7

Production of IRDIG35563 Bt Insecticidal Proteins and Variants in Dicot Plants

*Arabidopsis* Transformation.

*Arabidopsis thaliana* Col-01 was transformed using the floral dip method (Weigel and Glazebrook, 2002). The selected *Agrobacterium* colony was used to inoculate 1 mL to 15 mL cultures of YEP broth containing appropriate antibiotics for selection. The culture was incubated overnight at 28° C. with constant agitation at 220 rpm. Each culture was used to inoculate two 500 mL cultures of YEP broth containing appropriate antibiotics for selection and the new cultures were incubated overnight at 28° C. with constant agitation. The cells were pelleted at approximately 8700×g for 10 minutes at room temperature, and the resulting supernatant was discarded. The cell pellet was gently resuspended in 500 mL of infiltration media containing: ½× Murashige and Skoog salts (Sigma-Aldrich)/Gamborg's B5 vitamins (Gold BioTechnology, St. Louis, Mo.), 10% (w/v) sucrose, 0.044 µM benzylaminopurine (10 µL/L of 1 mg/mL stock in DMSO) and 300 µL/L Silwet L-77. Plants approximately 1 month old were dipped into the media for 15 seconds, with care taken to assure submergence of the newest inflorescence. The plants were then laid on their sides and covered (transparent or opaque) for 24 hours, washed with water, and placed upright. The plants were grown at 22° C., with a 16:8 light:dark photoperiod. Approximately 4 weeks after dipping, the seeds were harvested.

*Arabidopsis* Growth and Selection. Freshly harvested T1 seed was allowed to dry for at least 7 days at room temperature in the presence of desiccant. Seed was suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) was covered with fine vermiculite, sub-irrigated with Hoagland's solution (Hoagland and Arnon, 1950) until wet, then allowed to drain for 24 hours. Stratified seed was sown onto the vermiculite and covered with humidity domes (KORD Products, Bramalea, Ontario, Canada) for 7 days. Seeds were germinated and plants were grown in a Conviron (Models CMP4030 or CMP3244; Controlled Environments Limited, Winnipeg, Manitoba, Canada) under long day conditions (16:8 light:dark photoperiod) at a light intensity of 120-150 µmol/m$^2$ sec under constant temperature (22° C.) and humidity (40-50%). Plants were initially watered with Hoagland's solution and subsequently with deionized water to keep the soil moist but not wet.

The domes were removed 5-6 days post sowing and plants were sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays were performed at 5-7 day intervals. Survivors (plants actively growing) were identified 7-10 days after the final spraying and were transplanted into pots prepared with Sunshine Mix LP5. Transplanted plants were covered with a humidity dome for 3-4 days and placed in a Conviron under the above-mentioned growth conditions.

Those skilled in the art of dicot plant transformation will understand that other methods of selection of transformed plants are available when other plant expressible selectable marker genes (e.g. herbicide tolerance genes) are used. Table 3 shows the results (average score (SEM)) of *Arabidopsis* T1 bioassay against CEW, FAW, SAW, TBW, and SBL. Five events were generated for each construct and the average leaf damage score (5 leaf punches/event, 5 days post infestation) was recorded 5 weeks after germination. Construct design and numbering are reported in Table 4.

TABLE 3

| Protein | Construct | CEW | FAW | SAW | TBW | SBL |
|---|---|---|---|---|---|---|
| IRDIG35563 | pDAB134633 | 0.46 (0.22) | 0.42 (0.19) | 0.35 (0.15) | 0.45 (0.21) | 0.40 (0.19) |
|  | pDAB134634 | 0.1 (0) | 0.1 (0) | 0.1 (0) | 0.11 (0.01) | 0.1 (0) |
|  | pDAB134635 | 0.1 (0) | 0.1 (0) | 0.1 (0) | 0.30 (0.03) | 0.1 (0) |
|  | pDAB134636 | 0.1 (0) | 0.1 (0) | 0.1 (0) | 0.11 (0.01) | 0.1 (0) |
| Vip3Ab1 | Pos Control | 0.11 (0.01) | 0.1 (0) | 0.74 (0.06) | 0.1 (0) | 0.1 (0) |
| Col-0 | Neg Control | 1 (0) | 0.82 (0.07) | 0.61 (0.08) | 0.93 (0.04) | 0.98 (0.03) |

TABLE 4

| | |
|---|---|
| pDAB134633 | Agro Vector with AtUbi10 :: IRDIG35563.2 :: AtUbi10 + ZC21 + CsVMV :: DSM2 :: Orf1 |
| pDAB134634 | Agro Vector with AtUbi3 :: IRDIG35563.2 :: AtUbi3 + ZC21 + CsVMV :: DSM2 :: Orf1 |
| pDAB134635 | Agro Vector with AtAct2 :: IRDIG35563.2 :: AtAct2 + ZC21 + CsVMV :: DSM2 :: Orf1 |
| pDAB134636 | Agro Vector with GmCAB :: IRDIG35563.2 :: GmCAB + ZC21 + CsVMV :: DSM2 :: Orf1 |

Example 8

Transgenic *Glycine max* Comprising IRDIG35563

Ten to 20 transgenic $T_0$ *Glycine max* plants harboring expression vectors for nucleic acids comprising IRDIG35563 are generated, for example, by *Agrobacterium*-mediated transformation. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_2O$ for sixteen hours in the dark using a black box at 24° C.

Preparation of split-seed soybeans. The split soybean seed comprising a portion of an embryonic axis protocol requires preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation. The split soybean seeds comprising a partial portion of the embryonic axis are then immersed for about 30 minutes in a solution of *Agrobacterium tumefaciens* (e.g., strain EHA 101 or EHA 105) containing binary plasmid comprising IRDIG35563. The *Agrobacterium tumefaciens* solution is diluted to a final concentration of $\lambda$=0.6 $OD_{650}$ before immersing the cotyledons comprising the embryo axis.

Co-cultivation. Following inoculation, the split soybean seed is allowed to co-cultivate with the *Agrobacterium tumefaciens* strain for 5 days on co-cultivation medium (Wang, Kan. *Agrobacterium Protocols*. 2. 1. New Jersey: Humana Press, 2006. Print.) in a Petri dish covered with a piece of filter paper.

Shoot induction. After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SII medium supplemented with 6 mg/L glufosinate (LIBERTY®).

Shoot elongation. After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2EDTA$, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 µmol/m² sec.

Rooting. Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L Na$_2$EDTA, 20 g/L sucrose and 0.59 g/L MES, 50 mg/L asparagine, 100 mg/L L-pyroglutamic acid 7 g/L Noble agar, pH 5.6) in phyta trays.

Cultivation. Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 μmol/m² sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

Development and morphological characteristics of transgenic lines are compared with nontransformed plants. Plant root, shoot, foliage and reproduction characteristics are compared. Plant shoot characteristics such as height, leaf numbers and sizes, time of flowering, floral size and appearance are recorded. In general, there are no observable morphological differences between transgenic lines and those without expression of DIG proteins when cultured in vitro and in soil in the glasshouse.

Example 9

T0 Bioassays:

Five soybean events were generated for each construct and the average leaf damage score (5 leaf punches/event, 5 days post infestation) was recorded 5 weeks after germination. Construct design and numbering are reported in Table 4. Table 5 shows the results of soybean T0 bioassay against CEW, FAW, SAW, TBW, and SBL. The leaf damage grading scale utilizes and scoring system of 1 through 9, with 1 representing 88-100% damage. Deregulated transgenic soybean, Conkesta was used as a positive control. A non-transgenic soybean line was used as a negative control. The results for those events for which protein was detectable are presented in Table 5. Other test events produced inconclusive results due to, it is believed, environmental conditions experienced during transport. Table 6 presents the damage scale represented in Table 5.

TABLE 6

| Damage scale | Percent damage |
| --- | --- |
| 9 | 0 |
| 8 | 12.5 |
| 7 | 25 |
| 6.2 | 35 |
| 5 | 50 |
| 4 | 62.5 |
| 3 | 75 |
| 2 | 87.5 |
| 1 | 100 |

Example 10

Production of IRDIG35563

*Agrobacterium*-Mediated Transformation of Maize.

Seeds from a High II or B-104 F$_1$ cross (Armstrong et al., 1991) were planted into 5-gallon-pots containing a mixture of 95% Metro-Mix 360 soilless growing medium (Sun Gro Horticulture, Bellevue, Wash.) and 5% clay/loam soil. The plants were grown in a greenhouse using a combination of high pressure sodium and metal halide lamps with a 16:8 hour light:dark photoperiod. To obtain immature F$_2$ embryos for transformation, controlled sib-pollinations were performed. Immature embryos were isolated at 8-10 days post-pollination when embryos were approximately 1.0 to 2.0 mm in size.

Infection and co-cultivation Maize ears were surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension of *Agrobacterium* cells containing a superbinary vector were prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution was vortexed until a uniform suspension was achieved, and the concentration was adjusted to a final density of about 200 Klett units, using a Klett-Summerson colorimeter with a purple filter, or an optical density of approximately 0.4 at 550 nm. Immature embryos were isolated directly into a micro centrifuge tube containing 2 mL of the infection medium. The medium was removed and replaced with 1 mL

TABLE 5

| Event | Feature (RE) | BCW | CBW | CEW | FAW | SAW | SBL | TBW | VBC |
| --- | --- | --- | --- | --- | --- | --- | --- | --- | --- |
| Negative control | Negative | 1 | 3 | 1 | 1 | 1 | 1 | 1 | 1 |
| Negative control | Negative | 1 | 5 | 1 | 1 | 1 | 1 | 1 | 1 |
| Negative control | Negative | 1 | 5 | 1 | 1 | 5 | 2 | 1 | 1 |
| Negative control | Negative | 1 | 9 | 1 | 1 | 6.2 | 3 | 1 | 2 |
| Positive control | Positive | 1 | 8 | 8 | 9 | 7 | 9 | 9 | 9 |
| Positive control | Positive | 1 | 9 | 9 | 9 | 8 | 9 | 9 | 9 |
| Positive control | Positive | 3 | 9 | 9 | 9 | 8 | 9 | 9 | 9 |
| Positive control | Positive | 3 | 9 | 9 | 9 | 9 | 9 | 9 | 9 |
| 134635[8]-254 | AtActin2 | 7 | 9 | 7 | 9 | 9 | 9 | 4 | 9 |
| 134633[9]-209 | AtUbi10 | 8 | 8 | 9 | 9 | 8 | 9 | 9 | 9 |
| 134633[10]-224 | AtUbi10 | 8 | 5 | 7 | 9 | 9 | 9 | 4 | 8 |
| 134633[10]-212 | AtUbi10 | 5 | 8 | 8 | 9 | 6.2 | 9 | 5 | 8 | of the *Agrobacterium* solution with a density of 200 Klett units, and the *Agrobacterium* and embryo solution was incubated for 5 minutes at room temperature and then transferred to co-cultivation medium (LS Basal Medium, (containing N6 vitamins, 1.5 mg/L 2,4-D, 30.0 gm/L sucrose, 6 mM L-proline, 0.85 mg/L AgNO$_3$, 100 µM acetosyringone, and 3.0 gm/L Gellan gum (PhytoTechnology Laboratories., Lenexa, Kans.), pH 5.8) for 5 days at 25° C. under dark conditions.

After co-cultivation, the embryos were transferred to selective medium after which transformed isolates were obtained over the course of approximately 8 weeks. For selection of maize tissues transformed with a superbinary plasmid containing a plant expressible pat or bar selectable marker gene, an LS based medium (LS Basal medium, with 1×N6 vitamins, 1.5 mg/L 2,4-D, 0.5 gm/L MES (2-(N-morpholino)ethanesulfonic acid monohydrate; PhytoTechnology Laboratories., Lenexa, Kans.), 30.0 gm/L sucrose, 6 mM L-proline, 1.0 mg/L AgNO$_3$, 250 mg/L cefotaxime, 2.5 gm/L Gellan gum, pH 5.7) was used with Bialaphos (Gold BioTechnology, St. Louis, Mo.). The embryos were transferred to selection media containing 3 mg/L Bialaphos until embryogenic isolates were obtained. Recovered isolates were bulked up by transferring to fresh selection medium at 2-week intervals for regeneration and further analysis. Those skilled in the art of maize transformation will understand that other methods of selection of transformed plants are available when other plant expressible selectable marker genes (e.g. herbicide tolerance genes) are used.

Three constructs of IRDIG35563 contained in plasmids pDAB134672, pDAB134673, and pDAB134674 were transformed into maize (Table 7). T0 plants were regenerated and tested for their ability to control target insect pests.

TABLE 7

| Plasmid: | Description: |
|---|---|
| pDAB134672 | ZmUbi1-IRDIG35563.3-StPinII, ZC18, ZmUbi1-AAD1-ZmLip |
| pDAB134673 | ZmCAB-IRDIG35563.3-StPinII, ZC18, ZmUbi1-AAD1-ZmLip |
| pDAB134674 | OsUbi1-IRDIG35563.3-OsUbi1, ZC18, ZmUbi1-AAD1-ZmLip |

A 1.0×0.5 inch square leaf cutting was taken in duplicate from the V3 or V4 leaf of V5 T$_0$ transgenic plants. For each test, wild type plant leaf tissues were sampled first to prevent cross contamination of Bt toxins on the leaf edges, followed by the transformed plants. In each bioassay tray well (32-well trays and lids, CD International, Pitman, N.J.), 1 leaf cutting was placed on 2% water-agar (Fisher Scientific, Fair Lawn, N.J.) and this was replicated 2 times per insect species, per event and per construct.

Each well was infested with ten FAW neonates (24-48 hrs old) and sealed with a plastic perforated lid to allow for air exchange. The trays were placed at 28° C. (16:8 hr light: dark, 40% RH) and after 3 days they were graded for percent leaf damage. The percent leaf damage data was analyzed with ANOVA and mean separations with the Tukey-Kramer test when variances are homogenous by using JMP® Pro 9.0.1 (2010 SAS Institute Inc., Cary, N.C.). Results of FAW leaf damage in T0 maize expressing IRDIG35563 is presented in Table 8.

TABLE 8

| Construct | Events | Mean (Avg. Ding.) | Standard Error |
|---|---|---|---|
| pDAB134672 | 11 | 36.3 | 14.8 |
| pDAB134673 | 25 | 58 | 6.08 |
| pDAB134674 | 17 | 6.48 | 5.38 |
| B104 | 9 | 99.2 | 0.59 |
| Herculex | 9 | 22.2 | 4.65 |

Example 11

Regeneration and Seed Production.

For regeneration, the cultures are transferred to "28" induction medium (MS salts and vitamins, 30 gm/L sucrose, 5 mg/L Benzylaminopurine, 0.25 mg/L 2, 4-D, 3 mg/L Bialaphos, 250 mg/L cefotaxime, 2.5 gm/L Gellan gum, pH 5.7) for 1 week under low-light conditions (14 µEm$^{-2}$ s$^{-1}$) then 1 week under high-light conditions (approximately 89 µEm$^{-2}$ s$^{-1}$). Tissues are subsequently transferred to "36" regeneration medium (same as induction medium except lacking plant growth regulators). Plantlets 3-5 cm in length are transferred to glass culture tubes containing SHGA medium (Schenk and Hildebrandt salts and vitamins (1972); PhytoTechnology Laboratories., Lenexa, Kans.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

Example 12

Design of a plant-optimized version of the coding sequence for IRDIG35563. A DNA sequence having a plant codon bias was designed and synthesized to produce the IRDIG35563 protein in transgenic monocot and dicot plants. A codon usage table for maize (*Zea mays* L.) was calculated from 706 protein coding sequences (CDs) obtained from sequences deposited in GenBank. Codon usage tables for tobacco (*Nicotiana tabacum,* 1268 CDs), canola (*Brassica napus,* 530 CDs), cotton (*Gossypium hirsutum,* 197 CDs), and soybean (*Glycine max*; ca. 1000 CDs) were downloaded from data at the website http://www.kazusa.or.jp/codon/. A biased codon set that comprises highly used codons common to both maize and dicot datasets, in appropriate weighted average relative amounts, was calculated after omitting any redundant codon used less than about 10% of total codon uses for that amino acid in either plant type. To derive a plant optimized sequence encoding the IRDIG35563 protein, codon substitutions to the experimentally determined IRDIG35563 DNA sequence were made such that the resulting DNA sequence had the overall codon composition of the plant-optimized codon bias table. Further refinements of the sequence were made to eliminate undesirable restriction enzyme recognition sites, potential plant intron splice sites, long runs of A/T or C/G residues, and other motifs that might interfere with RNA stability, transcription, or translation of the coding region in plant cells. Other changes were made to introduce desired restriction enzyme recognition sites, and to eliminate long internal Open Reading Frames (frames other than +1). These changes were all made within the constraints of retaining the plant-biased codon composition. Synthesis of the designed sequence was performed by a commercial vendor (DNA2.0, Menlo Park, Calif.). Additional guidance regarding the production of synthetic genes can be found in, for example, WO 97/13402 and U.S. Pat. No. 5,380,831.

A maize-optimized high GC DNA sequence encoding IRDIG35563 is given in SEQ ID NO:3. A dicot-optimized DNA sequence encoding the full length IRDIG35563 is disclosed as SEQ ID NO:4.

Hybridization of immobilized DNA on Southern blots with radioactively labeled gene-specific probes may be performed by standard methods (Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology (See, e.g. Sambrook et al., supra.). In general, hybridization and subsequent washes may be carried out under stringent conditions that allow for detection of target sequences with homology to the claimed toxin encoding genes. For double-stranded DNA gene probes, hybridization may be carried out overnight at 20° C. to 25° C. below the $T_m$ of the DNA hybrid in 6×SSPE, 5×Denhardt's Solution, 0.1% SDS, 0.1 mg/mL denatured DNA [20×SSPE is 3M NaCl, 0.2 M NaHPO$_4$, and 0.02M EDTA (ethylenediamine tetra-acetic acid sodium salt); 100× Denhardt's Solution is 20 gm/L Polyvinylpyrollidone, 20 gm/L Ficoll type 400 and 20 gm/L BSA (fraction V)].

Washes may typically be carried out as follows:
a. Twice at room temperature for 15 minutes in 1×SSPE, 0.1% SDS (low stringency wash).
b. Once at 20° C. below the $T_m$ temperature for 15 minutes in 0.2×SSPE, 0.1% SDS (moderate stringency wash).

For oligonucleotide probes, hybridization may be carried out overnight at 10° C. to 20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(°C.) = 2(\text{number of T/A base pairs}) + 4(\text{number of G/C base pairs})$$

Washes may typically be carried out as follows:
a. Twice at room temperature for 15 minutes 1×SSPE, 0.1% SDS (low stringency wash).
b. Once at the hybridization temperature for 15 minutes in 1×SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

Example 13

Transformation of Additional Crop Species.

Cotton is transformed with IRDIG35563 (with or without a chloroplast transit peptide) to provide control of insect pests by utilizing a method known to those of skill in the art, for example, substantially the same techniques previously described in Example 14 of U.S. Pat. No. 7,838,733, or Example 12 of PCT International Patent Publication No. WO 2007/053482.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

BIBLIOGRAPHY

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) *Methods of Enzymology*, Vol. 100 Academic Press, New York pp. 266-285.

Crickmore, N., Baum, J., Bravo, A., Lereclus, D., Narva, K., Sampson, K., Schnepf, E., Sun, M. and Zeigler, D. R. "*Bacillus thuringiensis* toxin nomenclature" (2016) http://www.btnomenclature.info/

Huang, F., Rogers, L. B., Rhett, G. H. (2006) Comparative susceptibility of European corn borer, southwestern corn borer, and sugarcane borer (Lepidoptera: Crambidae) to Cry1Ab protein in a commercial *Bacillus thuringiensis* corn hybrid. J. Econ. Entomol. 99:194-202.

Lee, et. al. (2003) The Mode of Action of the *Bacillus thuringiensis* Vegetative Insecticidal Protein Vip3A Differs from That of Cry1Ab 6-Endotoxin. Appl. Environ. Microbiol. vol. 69 no. 8 4648-4657

Sambrook, J., Fritsch, E. F., Maniatis, T. (1989) *Molecular Cloning: A Laboratory Manual* (2nd ed., Cold Spring Harbor Laboratory Press, Plainview, N.Y.)

Tijssen, P. (1993) Laboratory Techniques in Biochemistry and Molecular Biology Hybridization with Nucleic Acid Probes, Part I, Chapter 2. P. C. van der Vliet (ed.), (Elsevier, N.Y.)

Wang, Kan. *Agrobacterium Protocols*. 2. 1. New Jersey: Humana Press, 2006. Print Weigel, D., Glazebrook, J. (eds.) (2002) Arabidopsis: A Laboratory Manual. Cold Spring Harbor Press, Cold Spring Harbor, N.Y., 354 pages.

Yu, C. G., Mullins, M. A., Warren, G. W., Koziel, M. G. and Estruch, J. J. (1997) The *Bacillus thuringiensis* vegetative insecticidal protein Vip3A lyses midgut epithelium cells of susceptible insects. Appl. Environ. Microbiol. February 1997; 63:2 532-6.

What is claimed is:

1. A recombinant nucleic acid construct comprising one or more heterologous regulatory elements that drive expression of a nucleic acid sequence encoding a polypeptide having insecticidal activity and having at least 96% sequence identity to the polypeptide sequence of SEQ ID NO: 2.

2. The construct of claim 1 in which the nucleic acid sequence is chosen from the group consisting of SEQ ID NO:1, SEQ ID NO:3, and SEQ ID NO:4.

3. An insecticidal chimeric toxin comprising residues 1 to 789 of SEQ ID NO:2.

4. An insecticidal chimeric toxin of claim 3 consisting of SEQ ID NO:2.

5. A plant or plant part comprising a nucleic acid construct of claim 1.

6. A plant or plant part comprising a nucleic acid construct of claim 2.

7. The plant part of claim 5 wherein the plant part is a seed.

8. The plant part of claim 6 wherein the plant part is a seed.

9. The plant or plant part of claim 5, wherein the nucleic acid construct encodes a chimeric toxin having insecticidal activity against one or more insects selected from *Spodoptera exigua* (Beet armyworm, BAW), *Spodoptera eridania* (Southern armyworm, SAW), *Spodoptera frugiperda* (Fall armyworm, FAW), resistant *Spodoptera frugiperda* (Fall armyworm, FAW), *Helicoverpa zea* (Corn earworm, CEW), *Pseudoplusia includens* (Soybean looper, SBL), *Anticarsia gemmatalis* (Velvetbean caterpillar, VBC), *Heliothis virescens* (Tobacco budworm, TBW), and *Helicoverpa armigera* (Cotton bollworm, CBW).

10. A plant or plant part of claim 6 wherein the nucleic acid construct encodes a chimeric toxin having insecticidal activity against one or more insects selected from *Spodoptera exigua* (Beet armyworm, BAW), *Spodoptera eridania* (Southern armyworm, SAW), *Spodoptera frugiperda* (Fall armyworm, FAW), resistant *Spodoptera frugiperda* (rFall armyworm, rFAW), *Helicoverpa zea* (Corn earworm, CEW), *Pseudoplusia includens* (Soybean looper, SBL), *Anticarsia gemmatalis* (Velvetbean caterpillar, VBC), *Heliothis virescens* (Tobacco budworm, TBW), and *Helicoverpa armigera* (Cotton bollworm, CBW).

11. A method for controlling susceptible insects comprising contacting said insect with an effective amount of a toxin of claim 3.

12. The method of claim 11 wherein the toxin is SEQ ID NO:2.

13. A method for controlling an insect pest population comprising contacting said pest population with a insecticidally effective amount of a toxin of claim 3.

14. The method of claim 13 wherein the insect pest population is selected from *Spodoptera exigua* (Beet armyworm, BAW), *Spodoptera eridania* (Southern armyworm, SAW), *Spodoptera frugiperda* (Fall armyworm, FAW), Cry1F resistant Fall Armyworm, *Helicoverpa zea* (Corn earworm, CEW), *Pseudoplusia includens* (Soybean looper, SBL), *Anticarsia gemmatalis* (Velvetbean caterpillar, VBC), *Heliothis virescens* (Tobacco budworm, TBW), and *Helicoverpa armigera* (Cotton bollworm, CBW).

15. A method for producing an insect resistant or insect tolerant plant comprising breeding a non-transgenic plant with a transgenic plant comprising a construct of claim 1 stably incorporated into the genome of the plant and selecting progeny containing the DNA construct of claim 1.

* * * * *

SEQUENCE LISTING

```
<160> NUMBER OF SEQ ID NOS: 4

<210> SEQ ID NO 1
<211> LENGTH: 2367
<212> TYPE: DNA
<213> ORGANISM: Unknown
<220> FEATURE:
<223> OTHER INFORMATION: Chimeric gene artificial sequence
```

```
<400> SEQUENCE: 1
atggcaaaca tgaacaacac caaactgaac gcgagagcgc tgcccagctt cattgattac      60
ttcaacggga tctacggttt tgcaactggc atcaaagaca tcatgaacat gatcttcaag     120
acggacacgg gtggcaacct tactctggac gagatcctca agaaccagca actcctcaat     180
gagatttctg ggaaactcga cggtgtcaac gggtctctga atgacttgat cgctcaaggc     240
aacttgaata ccgagctgtc caaggagata ctcaagatcg cgaacgagca gaatcaagtg     300
ttgaacgatg ttaacaacaa gttggatgcc atcaacacga tgctgcacat ctatctgcct     360
aagattactt ccatgctgtc cgacgtgatg aagcaaaact atgcgctgtc acttcaagtc     420
gagtacttgt ctaagcagct gaaggaaatc tcagacaagc tcgatgttat caacgtcaat     480
gttcttatca actctacttt gacggagatt actccagctt atcagcggat caagtatgtt     540
aacgagaagt tcgaagagct gactttcgca accgagacga ctctcaaggt caagaaggac     600
tcatcgccag ccgatatcct tgatgaattg actgagctta ctgagcttgc aaagtccgtg     660
accaagaatg acgtggacgg tttcgagttc tatcttaaca ccttccatga cgtgatggtt     720
ggcaacaatc tctttggcag atccgctctc aagactgcat cggaactgat cgccaaggag     780
aacgtcaaga cctccggttc agaggtgggg aacgtgtaca cttttctgat tgtcctcaca     840
gcgttgcaag ctaaggcctt cctcacactc accacatgtc gcaaacttt gggactcgca     900 gatatcgact acacttccat catgaacgaa catctgaaca aggagaagga ggagttcaga     960
gtgaacatct gccgactct ctccaatacg ttctcgaacc caaactacgc caaggtcaag    1020
ggttcagacg aggacgccaa gatgattgtt gaggctaaac tgggcacgc tctggttggg    1080 ttcgaaatct ccaacgattc catgacggtg cttaaggtgt atgaggctaa gctcaagcag    1140
aactatcaag ttgataagga cagcctctca gaggtgatct atagcgatat ggacaagttg    1200
ctctgtccgg atcagtccga gcaaatctac taccaacaa acatcgtgtt tcctaacgag    1260
tacgtcatca ccaagattga tttcactaag aagatgaaaa ctctcagata cgaagtcacg    1320
gcaaactctt atgactcatc gactggggaa atcgacctca acaagaagaa agtggagtcc    1380
tctgaggctg agtatcgcac cctctctgct aacaacgacg tgtgtacat gccactcggt    1440 gtcatttccg aaacattcct tacacccatc aacggtttcg gactgcaagc ggacgagaac    1500
tctcgcttga tcacactgac gtgcaagagc tatctgagag agctgcttct tgctacggat    1560
ctttccaaca aggagacaaa gctgatcgtt cctcccatca gcttcataag caacatcgtc    1620
gagaacggca tcttgaagg tgagaatctg gagccgtgga tcgcgaacaa caagaacgcc    1680
tacgttgacc acactggagg gatcaacggc accaaggtgc tctatgtcca caggatggc    1740 gagtttagcc agttcgtggg tggaaaactt aagtcaaaga ctgaatacgt catccagtac    1800
atcgtgaagg ggaaggcgtc aatctacttg aaagatgaaa atactggata tattctttat    1860
gaagatacaa ataatgattt agaagatttc caaactataa ctaaaaggtt cacaacagga    1920
actgatttaa tgagagtgta tttaatttta aaaagtcaaa gtggtcacga agcttgggga    1980
gataacttta caattttgga aattaagcct gcggaggctt tagtaagccc agaattgatt    2040
aatccgaatt cttggattac aactcaaggg gctagcattt caggagataa acttttttatt    2100 agcttgggga caaatgggac ctttagacaa aatctttcat taaacagtta ttcaacttat    2160
agtataagct ttactgcatc gggaccattt aatgtgacgg taagaaattc tagggaagta    2220
ttatatgaac gaaacaacct tatgtcttca actagtcata tttctgggga attcaaaact    2280
gaatccaata taccggatt atatgtagaa ctttcccgtc gttctggtgg tgctggtcat    2340
```

```
atatcatttg aaaacatttc tattaaa                                    2367
```

<210> SEQ ID NO 2
<211> LENGTH: 789
<212> TYPE: PRT
<213> ORGANISM: Unknown
<220> FEATURE:
<223> OTHER INFORMATION: Chimeric toxin artificial sequence

<400> SEQUENCE: 2

```
Met Ala Asn Met Asn Asn Thr Lys Leu Asn Ala Arg Ala Leu Pro Ser
1               5                   10                  15

Phe Ile Asp Tyr Phe Asn Gly Ile Tyr Gly Phe Ala Thr Gly Ile Lys
            20                  25                  30

Asp Ile Met Asn Met Ile Phe Lys Thr Asp Thr Gly Gly Asn Leu Thr
        35                  40                  45

Leu Asp Glu Ile Leu Lys Asn Gln Gln Leu Leu Asn Glu Ile Ser Gly
    50                  55                  60

Lys Leu Asp Gly Val Asn Gly Ser Leu Asn Asp Leu Ile Ala Gln Gly
65                  70                  75                  80

Asn Leu Asn Thr Glu Leu Ser Lys Glu Ile Leu Lys Ile Ala Asn Glu
                85                  90                  95

Gln Asn Gln Val Leu Asn Asp Val Asn Asn Lys Leu Asp Ala Ile Asn
            100                 105                 110

Thr Met Leu His Ile Tyr Leu Pro Lys Ile Thr Ser Met Leu Ser Asp
        115                 120                 125

Val Met Lys Gln Asn Tyr Ala Leu Ser Leu Gln Val Glu Tyr Leu Ser
    130                 135                 140

Lys Gln Leu Lys Glu Ile Ser Asp Lys Leu Asp Val Ile Asn Val Asn
145                 150                 155                 160

Val Leu Ile Asn Ser Thr Leu Thr Glu Ile Thr Pro Ala Tyr Gln Arg
                165                 170                 175

Ile Lys Tyr Val Asn Glu Lys Phe Glu Glu Leu Thr Phe Ala Thr Glu
            180                 185                 190

Thr Thr Leu Lys Val Lys Lys Asp Ser Ser Pro Ala Asp Ile Leu Asp
        195                 200                 205

Glu Leu Thr Glu Leu Thr Glu Leu Ala Lys Ser Val Thr Lys Asn Asp
    210                 215                 220

Val Asp Gly Phe Glu Phe Tyr Leu Asn Thr Phe His Asp Val Met Val
225                 230                 235                 240

Gly Asn Asn Leu Phe Gly Arg Ser Ala Leu Lys Thr Ala Ser Glu Leu
                245                 250                 255

Ile Ala Lys Glu Asn Val Lys Thr Ser Gly Ser Glu Val Gly Asn Val
            260                 265                 270

Tyr Asn Phe Leu Ile Val Leu Thr Ala Leu Gln Ala Lys Ala Phe Leu
        275                 280                 285

Thr Leu Thr Thr Cys Arg Lys Leu Leu Gly Leu Ala Asp Ile Asp Tyr
    290                 295                 300

Thr Ser Ile Met Asn Glu His Leu Asn Lys Glu Lys Glu Glu Phe Arg
305                 310                 315                 320

Val Asn Ile Leu Pro Thr Leu Ser Asn Thr Phe Ser Asn Pro Asn Tyr
                325                 330                 335

Ala Lys Val Lys Gly Ser Asp Glu Asp Ala Lys Met Ile Val Glu Ala
            340                 345                 350
```

```
Lys Pro Gly His Ala Leu Val Gly Phe Glu Ile Ser Asn Asp Ser Met
            355                 360                 365

Thr Val Leu Lys Val Tyr Glu Ala Lys Leu Lys Gln Asn Tyr Gln Val
    370                 375                 380

Asp Lys Asp Ser Leu Ser Glu Val Ile Tyr Ser Asp Met Asp Lys Leu
385                 390                 395                 400

Leu Cys Pro Asp Gln Ser Glu Gln Ile Tyr Tyr Thr Asn Asn Ile Val
                405                 410                 415

Phe Pro Asn Glu Tyr Val Ile Thr Lys Ile Asp Phe Thr Lys Lys Met
            420                 425                 430

Lys Thr Leu Arg Tyr Glu Val Thr Ala Asn Ser Tyr Asp Ser Ser Thr
    435                 440                 445

Gly Glu Ile Asp Leu Asn Lys Lys Val Glu Ser Ser Glu Ala Glu
    450                 455                 460

Tyr Arg Thr Leu Ser Ala Asn Asn Asp Gly Val Tyr Met Pro Leu Gly
465                 470                 475                 480

Val Ile Ser Glu Thr Phe Leu Thr Pro Ile Asn Gly Phe Gly Leu Gln
                485                 490                 495

Ala Asp Glu Asn Ser Arg Leu Ile Thr Leu Thr Cys Lys Ser Tyr Leu
            500                 505                 510

Arg Glu Leu Leu Leu Ala Thr Asp Leu Ser Asn Lys Glu Thr Lys Leu
    515                 520                 525

Ile Val Pro Pro Ile Ser Phe Ile Ser Asn Ile Val Glu Asn Gly Asn
    530                 535                 540

Leu Glu Gly Glu Asn Leu Glu Pro Trp Ile Ala Asn Asn Lys Asn Ala
545                 550                 555                 560

Tyr Val Asp His Thr Gly Gly Ile Asn Gly Thr Lys Val Leu Tyr Val
                565                 570                 575

His Lys Asp Gly Glu Phe Ser Gln Phe Val Gly Gly Lys Leu Lys Ser
            580                 585                 590

Lys Thr Glu Tyr Val Ile Gln Tyr Ile Val Lys Gly Lys Ala Ser Ile
    595                 600                 605

Tyr Leu Lys Asp Glu Asn Thr Gly Tyr Ile Leu Tyr Glu Asp Thr Asn
610                 615                 620

Asn Asp Leu Glu Asp Phe Gln Thr Ile Thr Lys Arg Phe Thr Thr Gly
625                 630                 635                 640

Thr Asp Leu Met Arg Val Tyr Leu Ile Leu Lys Ser Gln Ser Gly His
                645                 650                 655

Glu Ala Trp Gly Asp Asn Phe Thr Ile Leu Glu Ile Lys Pro Ala Glu
            660                 665                 670

Ala Leu Val Ser Pro Glu Leu Ile Asn Pro Asn Ser Trp Ile Thr Thr
    675                 680                 685

Gln Gly Ala Ser Ile Ser Gly Asp Lys Leu Phe Ile Ser Leu Gly Thr
    690                 695                 700

Asn Gly Thr Phe Arg Gln Asn Leu Ser Leu Asn Ser Tyr Ser Thr Tyr
705                 710                 715                 720

Ser Ile Ser Phe Thr Ala Ser Gly Pro Phe Asn Val Thr Val Arg Asn
                725                 730                 735

Ser Arg Glu Val Leu Tyr Glu Arg Asn Asn Leu Met Ser Ser Thr Ser
            740                 745                 750

His Ile Ser Gly Glu Phe Lys Thr Glu Ser Asn Asn Thr Gly Leu Tyr
    755                 760                 765

Val Glu Leu Ser Arg Arg Ser Gly Gly Ala Gly His Ile Ser Phe Glu
```

Asn Ile Ser Ile Lys
785

<210> SEQ ID NO 3
<211> LENGTH: 2370
<212> TYPE: DNA
<213> ORGANISM: Unknown
<220> FEATURE:
<223> OTHER INFORMATION: Maize codon optimized artificial sequence

<400> SEQUENCE: 3

| | | | | |
|---|---|---|---|---|
| atggcgaaca | tgaataatac | taaattaaac | gcccgcgcgc | tgcccagctt | catcgactac | 60 |
| ttcaacggca | tctacggctt | cgccaccggc | atcaaggaca | tcatgaacat | gatcttcaag | 120 |
| accgacaccg | gcggcaacct | gaccctggac | gagatcctga | agaaccagca | gctgctgaac | 180 |
| gagatcagcg | gcaagctgga | cggcgtgaac | ggcagcctga | cgacctgat | cgcgcaaggc | 240 |
| aaccttaata | cagagctgtc | caaggagatc | ctgaagatcg | ccaacgagca | gaatcaagtg | 300 |
| ctgaacgacg | tgaacaacaa | gctggacgcc | atcaacacca | tgctgcacat | ctacctgccc | 360 |
| aagatcacct | caatgctgag | cgacgtgatg | aagcagaact | acgccctgtc | cctgcaagtg | 420 |
| gagtacctgt | ccaagcagct | gaaggagatc | tccgacaagc | tggacgtgat | caacgtgaac | 480 |
| gtgctgatca | cagcaccct | gaccgagatc | accccgcgt | accagaggat | taaatacgtg | 540 |
| aatgaaaagt | cgaggaatt | aaccttcgcc | accgagacga | ccctgaaggt | gaagaaggac | 600 |
| tccagcccgg | ccgacatcct | ggacgagctg | accgaattaa | ccgagctggc | gaagtccgtg | 660 |
| accaagaacg | acgtggacgg | cttcgagttc | tacctgaata | cattccacga | cgtgatggtg | 720 |
| ggcaataatc | tgttcggccg | ctccgccctg | aagaccgcct | ccgaattaat | cgctaaggag | 780 |
| aacgtgaaga | ccagcggctc | agaggtgggc | aacgtgtaca | cttcctgat | cgtgctgacc | 840 |
| gccctgcaag | ccaaggcgtt | cctgaccctg | accacctgta | ggaagctgct | gggcctggcg | 900 |
| gacatcgact | atacatccat | catgaacgag | cacctgaaca | aggagaagga | ggagttccgc | 960 |
| gtgaacatcc | tgcccaccct | gtccaacacc | ttctccaacc | cgaactacgc | caaggtgaag | 1020 |
| ggctccgacg | aggacgccaa | gatgatcgtg | gaggccaagc | ccggcacgc | gctggtgggc | 1080 |
| ttcgagatct | ccaacgactc | catgaccgta | ttaaaggtgt | acgaggccaa | gctgaagcag | 1140 |
| aactaccaag | tggacaagga | cagcctgagc | gaggtgatct | cagcgacat | ggacaagctg | 1200 |
| ctgtgcccgg | accagtccga | gcagatctac | taccaata | atatcgtgtt | ccccaacgag | 1260 |
| tacgtgatca | ccaagatcga | cttcaccaag | aagatgaaaa | ccctgcgcta | cgaggtgacc | 1320 |
| gcgaacagct | acgactcctc | caccggcgag | atcgacctga | caagaagaa | ggtggaatca | 1380 |
| agcgaggcgg | agtaccgcac | cctgagcgcc | aataatgacg | cgtgtacat | gccgctgggc | 1440 |
| gtgatctccg | aaaccttcct | gacccccaatt | aatggctttg | gcctgcaagc | ggatgaaaac | 1500 |
| tcaagattaa | tcaccctgac | ctgcaagagc | tacctgcgcg | agctgctgct | ggccaccgac | 1560 |
| ctgtccaata | agaaacgaa | actgatcgtg | ccgcccatca | gcttcatcag | caacatcgtg | 1620 |
| gagaacggca | acctggaggg | cgagaacctg | gagccctgga | tcgccaacaa | caagaacgcc | 1680 |
| tacgtggacc | acaccggcgg | catcaacggc | accaaggtgt | gtacgtgca | aggacggc | 1740 |
| gagttcagcc | agttcgtggg | cggcaagctg | aagtccaaga | ccgagtacgt | gatccagtac | 1800 |
| atcgtgaagg | gcaaggccag | catctacctg | aaggatgaaa | ataccggcta | catcctgtac | 1860 |
| gaggacacca | taatgaccct | ggaggacttc | cagaccatca | ccaagaggtt | caccaccggc | 1920 |

| accgacctga tgcgcgtgta cctgatcctg aagtcccagt ccggccacga ggcgtggggc | 1980 |
| gacaacttca ccatcctgga aataaagccg gccgaggccc tggtgagccc ggagctgatt | 2040 |
| aatccgaaca gctggatcac cacccaaggc gccagcatca gcggcgacaa gctgttcatc | 2100 |
| agcctgggca ccaacggcac ctttaggcag aacctgtcat aaactcata cagcacctac | 2160 |
| tccatcagct tcaccgcctc cggcccgttc aacgtgaccg tgaggaactc gagggaggtg | 2220 |
| ctgtacgaga ggaacaacct gatgagctcc acctcccata tcagcggcga gttcaagacc | 2280 |
| gagtccaata taccggcct gtacgtggag ctgtcccgta ggagcggcgg cgcgggccac | 2340 |
| atcagcttcg agaacatctc cattaaataa | 2370 |

```
<210> SEQ ID NO 4
<211> LENGTH: 2370
<212> TYPE: DNA
<213> ORGANISM: Unknown
<220> FEATURE:
<223> OTHER INFORMATION: Soybean codon optimized artificial sequence

<400> SEQUENCE: 4
```

| atggctaaca tgaataatac taaattaaac gctcgtgctt tgccctcttt cattgactac | 60 |
| ttcaacggaa tctacggttt cgccactggc atcaaagaca tcatgaacat gatcttcaag | 120 |
| accgacaccg gtggcaacct cacccttgat gagattctca agaaccagca gctcctcaac | 180 |
| gagatttctg ggaaactcga tggtgtcaac ggctctctca atgacttgat tgctcaaggc | 240 |
| aacttgaata cagaactttc caaggagatt ctcaagattg ccaacgaaca gaatcaagtg | 300 |
| ttgaacgacg tcaacaacaa gttggatgcc atcaacacca tgcttcacat ctatcttccc | 360 |
| aagatcactt ccatgctcag cgatgtgatg aagcagaact acgctctttc ccttcaagtt | 420 |
| gagtacttgt ccaagcagtt gaaggaaatc tccgacaagc ttgatgtcat caacgtcaat | 480 |
| gttctcatca actctacttt gaccgagatc accccagctt atcagaggat taaatatgtg | 540 |
| aatgaaaagt tgaagaatt aactttcgca accgagacta ccctcaaggt caagaaggac | 600 |
| tcaagcccag ctgacatcct tgatgaattg accgaattaa ctgagcttgc aaagtctgtg | 660 |
| accaagaatg atgttgacgg tttcgagttc tatctcaata catttcacga cgtcatggtt | 720 |
| ggcaataatc tctttggacg ttccgctctc aagactgcat ccgaattaat cgccaaggag | 780 |
| aacgtcaaga cctctggctc agaggtgggc aacgtgtaca acttcttgat tgttctcaca | 840 |
| gcccttcaag ccaaggcttt cctcacactc accacatgta ggaaactttt gggacttgct | 900 |
| gacattgact atacatccat catgaacgaa cacctcaaca aggagaagga agagttaga | 960 |
| gtgaacatct tgcctactct ctccaatacc ttctccaatc caaactatgc caaggtcaag | 1020 |
| ggttcagacg aggacgccaa gatgattgtt gaggccaagc tgggcacgc tcttgttggt | 1080 |
| tttgaaatct ccaatgactc catgaccgta ttaaaggtgt acgaggccaa gctcaagcag | 1140 |
| aactatcaag ttgacaagga cagcctctca gaggtgatct acagcgacat ggacaagctt | 1200 |
| ctctgcccag accagtccga gcagatctac tacaccaata atattgtctt tccaaacgag | 1260 |
| tacgtcatta ccaagattga tttcacaaag aagatgaaaa cccttcgtta cgaagtcacc | 1320 |
| gcaaactctt acgactcttc cactggggag attgacctca caagaagaa agttgaatca | 1380 |
| agcgaggctg agtataggac cctctctgcc aataatgacg gtgtgtacat gccacttggt | 1440 |
| gtcatttccg aaacatttct cactccaatt aatggttttg gactccaagc agatgaaaac | 1500 |
| tcaagattaa ttacactcac ctgcaagagc tacttgagag agctccttct tgcaaccgat | 1560 |
| cttttccaata aagagacaaa gttgattgtt cctcccatca gcttcatcag caacattgtt | 1620 |

-continued

```
gagaatggca atcttgaagg tgagaacctt gagccttgga ttgccaacaa caagaacgcc   1680
tacgttgatc atactggagg gatcaacggc accaaggttc tctatgttca caaggatggc   1740
gagtttagcc agtttgtggg tggaaagttg aagtcaaaga ctgaatacgt cattcagtac   1800
attgtgaaag gcaaggcctc aatctacttg aaagatgaaa atactggcta catcctttac   1860
gaagacacaa ataatgatct cgaagatttc cagaccatca caaagaggtt cacaactgga   1920
actgatctca tgagagtgta cttgatcttg aaaagccagt ccggtcacga agcttgggga   1980
gacaacttca ccatccttga aataaagcct gccgaggctt tggtcagccc agaattgatt   2040
aatcccaact cttggattac aacccaaggt gccagcattt ctggagacaa acttttcatt   2100
agcttgggga caaatgggac cttcagacag aatctttcat taaactctta ctcaacctac   2160
tccatcagct tcactgcatc cggacccttc aatgtgaccg tgaggaattc aagggaagtc   2220
ttgtacgaaa ggaacaacct catgtcttca acctcccata tcagcggaga gttcaaaacc   2280
gaatccaata ataccggatt gtacgttgaa ctttcccgtc gttctggtgg tgctggtcac   2340
atttcttttg aaaacatttc cattaaataa                                    2370
```